(12) United States Patent
Heil et al.

(10) Patent No.: US 10,381,575 B2
(45) Date of Patent: Aug. 13, 2019

(54) MATERIALS FOR ELECTRONIC DEVICES

(71) Applicant: Merck Patent GmbH, Darmstadt (DE)

(72) Inventors: Holger Heil, Frankfurt am Main (DE);
Anja Gerhard, Egelsbach (DE);
Fabrice Eckes, Darmstadt (DE);
Amandine Darsy, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 520 days.

(21) Appl. No.: 14/782,816

(22) PCT Filed: Mar. 10, 2014

(86) PCT No.: PCT/EP2014/000613
§ 371 (c)(1),
(2) Date: Oct. 7, 2015

(87) PCT Pub. No.: WO2014/166571
PCT Pub. Date: Oct. 16, 2014

(65) Prior Publication Data
US 2016/0133854 A1 May 12, 2016

(30) Foreign Application Priority Data
Apr. 8, 2013 (EP) .................................... 13001798

(51) Int. Cl.
| C07D 491/107 | (2006.01) |
| H01L 51/00 | (2006.01) |
| C09K 11/06 | (2006.01) |
| C07D 405/14 | (2006.01) |
| C07D 487/14 | (2006.01) |
| C07D 215/30 | (2006.01) |
| C07D 255/04 | (2006.01) |
| C07D 245/04 | (2006.01) |
| H01L 51/50 | (2006.01) |

(52) U.S. Cl.
CPC ........ *H01L 51/0072* (2013.01); *C07D 215/30* (2013.01); *C07D 245/04* (2013.01); *C07D 255/04* (2013.01); *C07D 405/14* (2013.01); *C07D 487/14* (2013.01); *C07D 491/107* (2013.01); *C09K 11/06* (2013.01); *H01L 51/006* (2013.01); *H01L 51/0054* (2013.01); *H01L 51/0061* (2013.01); *H01L 51/0071* (2013.01); *H01L 51/0073* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/1096* (2013.01); *H01L 51/5012* (2013.01); *Y02E 10/549* (2013.01)

(58) Field of Classification Search
CPC combination set(s) only.
See application file for complete search history.

(56) References Cited

U.S. PATENT DOCUMENTS

| 2002/0058155 A1* | 5/2002 | Guofang | C07D 257/10 428/690 |
| 2007/0009758 A1* | 1/2007 | Funahashi | C07C 211/61 428/690 |
| 2007/0252511 A1 | 11/2007 | Funahashi | |
| 2007/0292714 A1 | 12/2007 | Funahashi | |
| 2009/0029276 A1 | 1/2009 | Coggan et al. | |
| 2011/0156011 A1 | 6/2011 | Bin et al. | |
| 2011/0193064 A1 | 8/2011 | Funahashi | |
| 2012/0032152 A1 | 2/2012 | Kim et al. | |
| 2013/0193382 A1 | 8/2013 | Buesing et al. | |

FOREIGN PATENT DOCUMENTS

| JP | 04-175395 | 6/1992 |
| JP | 05-323635 | 12/1993 |
| JP | 2012512243 A | 5/2012 |
| WO | 2008136522 A1 | 7/2010 |
| WO | 2012048780 A1 | 4/2012 |

OTHER PUBLICATIONS

International Search Report for International Application No. PCT/EP2014/000613; International Filing Date Mar. 10, 2014.
Song, et al., "A Cyclic Triphenylamine Dimer for Organic Field-Effect Transistors with High Performance," J. Am. Chem. Soc., vol. 128, pp. 15940-15941 (2006).
Yu, et al., "Basket-shaped quinacridone cyclophanes: synthesis, solid-state structures, and properties," New J. Chem., vol. 34, pp. 2213-2219 (2010).
Office Action issued in Japanese Patent Application Serial No. 2016-506796, dated Feb. 13, 2018.

* cited by examiner

*Primary Examiner* — Jennifer A Chriss
*Assistant Examiner* — Sean M DeGuire
(74) *Attorney, Agent, or Firm* — Kim IP Law Group PLLC

(57) ABSTRACT

The present invention relates to a compound, comprising a pyrene skeleton and arylamino groups, according to formula (I). The compound is suitable for use as a functional material in electronic devices.

(I)

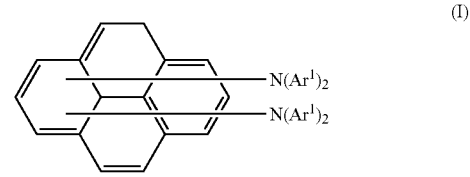

14 Claims, No Drawings

MATERIALS FOR ELECTRONIC DEVICES

RELATED APPLICATIONS

This application is a national stage entry, filed pursuant to 35 U.S.C. § 371, of PCT/EP2014/000613, filed Mar. 10, 2014, which claims the benefit of European Patent Application No. 13001798.1, filed Apr. 8, 2013, which is incorporated herein by reference in its entirety.

The present invention relates to a compound of a formula (I). The compound is a pyrene which contains at least two arylamino groups which are connected to one another via a bridging group. The compound is suitable for use as functional material in an electronic device, in particular an organic electroluminescent device (OLED).

In accordance with the present application, the term electronic device is generally taken to mean electronic devices which comprise organic materials. It is preferably taken to mean OLEDs and further embodiments of electronic devices comprising organic materials which are disclosed later.

In general, the term OLED is taken to mean an electronic device which comprises at least one organic material and emits light on application of an electrical voltage. The precise structure of OLEDs is described, inter alia, in U.S. Pat. Nos. 4,539,507, 5,151,629, EP 0676461 and WO 98/27136.

Further improvements are necessary with respect to the performance data of the electronic devices, in particular in view of broad commercial use, for example in displays or as light sources. Of particular importance in this connection are the lifetime, the efficiency and the operating voltage of the electronic devices and the colour values achieved. In particular in the case of blue-emitting OLEDs, there is potential for improvement with respect to the lifetime of the devices and the colour values achieved of the emitted light.

An important starting point for achieving the said improvements is the choice of the emitting compound employed in the electronic device.

A multiplicity of compounds are known from the prior art as blue-fluorescent emitters, in particular arylamines containing one or more condensed aryl groups.

For example, EP 1604974 and US 2011/0156011 disclose diarylaminopyrene compounds which are suitable as blue-emitting compounds in electronic devices. The compounds contain a central pyrene group to which one, two or more diarylamino groups are bonded. Furthermore, US 2012/0032152 discloses diarylaminopyrene compounds which are suitable as blue-emitting compounds in electronic devices. The compounds contain a pyrene group to which an aryl group is bonded, to which a diarylamino group is in turn bonded. A diarylamino group is bonded as second substituent to the pyrene group.

However, there is in general a need for alternative functional materials which are suitable for use in electronic devices, in particular OLEDs. The technical requirements of the materials, in particular in the function as blue-emitting compounds, have also not yet been satisfied entirely satisfactorily. A specific technical object can therefore be the improvement of the performance data of the electronic device, including, in particular, lifetime, deep-blue colour coordinates of the emitted light and/or power efficiency.

There is a need for functional materials for OLEDs which have deep-blue colour coordinates on use as emitters, and which have a narrow emission band. The latter is particularly important in the case of combination of a plurality of emitter materials having a different position of their emission bands whose emitted light is mixed, for example to give white light.

It is also of interest to increase the temperature stability of the compounds for use in electronic devices, on the one hand owing to the increased temperature of the devices in operation, on the other hand owing to the very high temperatures which occur during purification of the materials by sublimation and during the application of the materials by gas-phase deposition in the production process of the electronic device.

In summary, the technical object is thus to provide alternative functional materials for use in electronic devices. In particular, the object is to provide materials which have improved properties and/or effect improved properties of the electronic device comprising the material, in particular in the above-mentioned aspects.

In spite of the wide variety of pyrenylarylamine compounds which have been proposed to date for use in electronic devices, the prior art has to date in no case taught to connect the arylamino groups which are bonded to the central pyrene skeleton to one another via a bridging group.

Surprisingly, it has now been found that pyrene compounds which contain at least two diarylamino groups, where the diarylamino groups are connected to one another via a bridging group, are eminently suitable for use as functional materials in electronic devices and thus achieve the above-mentioned technical object.

They preferably have deep-blue colour coordinates, a small width of the emission band, and/or high temperature stability, and/or result in advantageous performance data on use in an electronic device.

The invention thus relates to a compound of a formula (I)

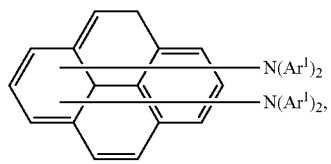

formula (I)

where the pyrene group may be substituted by a radical $R^1$ at each free position, and where:

in the formula (I), at least one group $Ar^1$ which is a constituent of a group $N(Ar^1)_2$ is linked to another group $Ar^1$ which is a constituent of another group $N(Ar^1)_2$ via a group X;

$Ar^1$ is on each occurrence, identically or differently, an aromatic or heteroaromatic ring system having 6 to 30 aromatic ring atoms, which may be substituted by one or more radicals $R^3$, where groups $Ar^1$ may be linked here via groups X;

X is on each occurrence, identically or differently, a single bond, or a divalent group selected from an aryl or heteroaryl group having 6 to aromatic ring atoms, which may be substituted by one or more radicals $R^2$, or $BR^2$, $C(R^2)_2$, $-R^2C=CR^2-$, $C(=O)$, $Si(R^2)_2$, $NR^2$, $PR^2$, $P(=O)R^2$, O, S, $S(=O)$, $S(=O)_2$, or a combination of 2, 3, 4 or 5 identical or different divalent groups of those mentioned;

$R^1$ is on each occurrence, identically or differently, H, D, F, $C(=O)R^4$, CN, $Si(R^4)_3$, $N(Ar^1)_2$, $N(R^4)_2$, $P(=O)(R^4)_2$, $OAr^1$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, $SO$ or $SO_2$, or an aromatic or heteroaromatic ring system having 5 to aromatic ring atoms, which may in each case be substituted by one or more radicals $R^4$, where two or more radicals $R^1$ may be linked to one another and may form a ring;

$R^2$ is on each occurrence, identically or differently, H, D, F, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, $SO$ or $SO_2$, or an aromatic or heteroaromatic ring system having 5 to aromatic ring atoms, which may in each case be substituted by one or more radicals $R^4$, where two or more radicals $R^2$ may be linked to one another and may form a ring;

$R^3$ is on each occurrence, identically or differently, H, D, F, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, $SO$ or $SO_2$, or an aromatic or heteroaromatic ring system having 5 to aromatic ring atoms, which may in each case be substituted by one or more radicals $R^4$, where two or more radicals $R^3$ may be linked to one another and may form a ring;

$R^4$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^4$ here may be linked to one another and may form a ring.

The depiction of the bonding of the groups $N(Ar^1)_2$ in formula (I) to the pyrene means that the bonding may take place at any desired free position of the pyrene.

The following numbering of the pyrene is used:

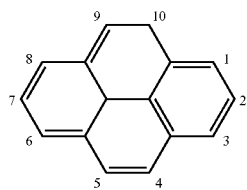 [SMILES: C1=CC2=CCc3cccc4c3C2C(=C1)C=C4]

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexyloxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following scheme:

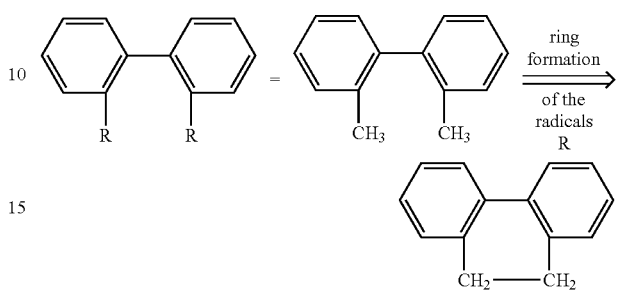

Furthermore, however, the above-mentioned formulation is also intended to be taken to mean that, in the case where one of the two radicals represents hydrogen, the second radical is bonded at the position at which the hydrogen atom was bonded, with formation of a ring. This is intended to be illustrated by the following scheme:

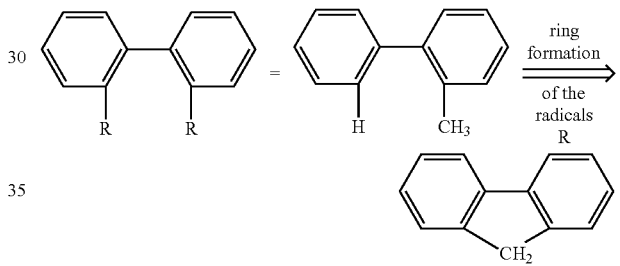

In a preferred embodiment, the group X is on each occurrence, identically or differently, a single bond or a divalent group selected from an aryl or heteroaryl group having 6 to 14 aromatic ring atoms, which may be substituted by one or more radicals $R^2$, or $C(R^2)_2$, $C(=O)$, $Si(R^2)_2$, $NR^2$, O or S, or a combination of 2, 3 or 4 identical or different divalent groups of these.

X is particularly preferably on each occurrence, identically or differently, a single bond or a divalent group selected from an aryl or heteroaryl group having 6 aromatic ring atoms, which may be substituted by one or more radicals $R^2$, or $C(R^2)_2$, $C(=O)$, $Si(R^2)_2$, $NR^2$, O, S, —$C(R^2)_2$—$C(R^2)_2$—, or —$NR^1$—$(Ar^2)_n$—$NR^1$—, where n is equal to 1 or 2, and $Ar^2$ is an aryl or heteroaryl group having 6 aromatic ring atoms, which may be substituted by one or more radicals $R^2$.

X is very particularly preferably on each occurrence, identically or differently, a divalent group selected from $C(R^2)_2$, $NR^2$, O and S, even more preferably a divalent group selected from $C(R^2)_2$ and $NR^2$.

In a preferred embodiment of the invention, groups $R^2$ which are bonded to the same atom of a unit X form a ring with one another, so that a spiro atom forms. This is preferably a five-membered ring or a six-membered ring, where the groups $R^2$ are preferably aryl groups or alkyl groups. The group X is in these cases very particularly preferably selected from groups of the following formulae (X-1) to (X-10)

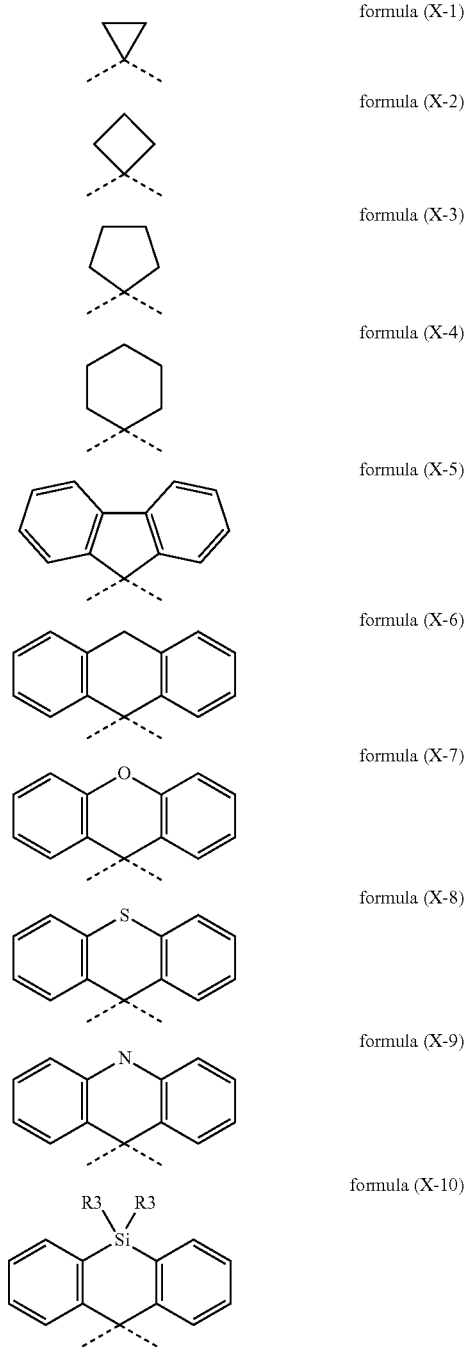

formula (X-1)
formula (X-2)
formula (X-3)
formula (X-4)
formula (X-5)
formula (X-6)
formula (X-7)
formula (X-8)
formula (X-9)
formula (X-10)

where the groups depicted may optionally be substituted by one or more radicals $R^4$ in the positions depicted as unsubstituted, and where the dashed lines represent bonds to the remainder of the compound.

The compound of the formula (I) preferably contains precisely one or precisely 2 groups X. Correspondingly, precisely 1 pair of groups $Ar^1$ or precisely 2 pairs of groups $Ar^1$ are preferably linked to one another via in each case one group X.

In a preferred embodiment, $Ar^1$ is on each occurrence, identically or differently, an aromatic or heteroaromatic ring system having 6 to 18 aromatic ring atoms, which may be substituted by one or more radicals $R^3$. $Ar^1$ is particularly preferably on each occurrence, identically or differently, an aromatic ring system having 6 to 12 aromatic ring atoms, which may be substituted by one or more radicals $R^3$. $Ar^1$ is very particularly preferably phenyl, which may be substituted by one or more radicals $R^3$.

Two groups $Ar^1$ bonded to the same nitrogen atom may in each case be connected via a single bond. A carbazole is preferably formed here.

$R^1$ is preferably on each occurrence, identically or differently, H, D, F, CN, $Si(R^4)_3$, $N(Ar^1)_2$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more $CH_2$ groups in the above-mentioned groups may be replaced by —C≡C—, —$R^4$C=C$R^4$—, Si($R^4)_2$, C=O, C=N$R^4$, —N$R^4$—, —O—, —S—, —C(=O)O— or —C(=O)N$R^4$—, or an aromatic or heteroaromatic ring system having 5 to 20 aromatic ring atoms, which may in each case be substituted by one or more radicals $R^4$, where two or more radicals $R^1$ may be linked to one another and may form a ring.

The pyrene group is particularly preferably substituted by at least one radical $R^1$ which is not equal to H. The pyrene group is very particularly preferably substituted by at least one $R^1$ which is selected from a straight-chain alkyl group having 1 to 8 C atoms or a branched or cyclic alkyl group having 3 to 8 C atoms, where the alkyl groups may be substituted by one or more radicals $R^4$, or from an aryl or heteroaryl group having 6 to 14 aromatic ring atoms, which may be substituted by one or more radicals $R^4$.

It is preferred, in the case where the groups $N(Ar^1)_2$ are bonded in positions selected from positions 6, 7 and 8, that the compound contains, in position 2 of the pyrene skeleton, a group $R^1$ which is not equal to H, and which is preferably selected from a straight-chain alkyl group having 1 to 8 C atoms or a branched or cyclic alkyl group having 3 to 8 C atoms, where the alkyl groups may be substituted by one or more radicals $R^4$, or from an aryl or heteroaryl group having 6 to 14 aromatic ring atoms, which may be substituted by one or more radicals $R^4$.

It is preferred, in the case where the groups $N(Ar^1)_2$ are bonded in positions selected from positions 1, 2 and 3, that the compound contains, in position 7 of the pyrene skeleton, a group $R^1$ which is not equal to H, and which is preferably selected from a straight-chain alkyl group having 1 to 8 C atoms or a branched or cyclic alkyl group having 3 to 8 C atoms, where the alkyl groups may be substituted by one or more radicals $R^4$, or from an aryl or heteroaryl group having 6 to 14 aromatic ring atoms, which may be substituted by one or more radicals $R^4$.

$R^2$ is preferably on each occurrence, identically or differently, F, CN, a straight-chain alkyl group having 1 to 20 C atoms or a branched or cyclic alkyl group having 3 to 20 C atoms, where the above-mentioned groups may each be substituted by one or more radicals $R^4$ and where one or more $CH_2$ groups in the above-mentioned groups may be replaced by —C≡C—, —$R^4$C=C$R^4$—, Si($R^4)_2$, C=O, C=N$R^4$, —N$R^4$—, —O—, —S—, —C(=O)O— or —C(=O)N$R^4$—, or an aromatic or heteroaromatic ring system having 5 to 20 aromatic ring atoms, which may in each case be substituted by one or more radicals $R^4$, where two or more radicals $R^2$ may be linked to one another and may form a ring.

Radicals $R^2$ on a group X which represents $C(R^2)_2$ or $Si(R^2)_2$ are particularly preferably selected from a straight-chain alkyl group having 1 to 8 C atoms or a branched or cyclic alkyl group having 3 to 8 C atoms, where the alkyl groups may be substituted by one or more radicals R⁴, or from an aryl or heteroaryl group having 6 to 14 aromatic ring atoms, which may be substituted by one or more radicals R⁴. Groups R² of this type are preferably linked to one another, particularly preferably in such a way that a group of one of the formulae (X-1) to (X-10) forms.

Radicals R² on a group X which represents NR² or PR² or P(=O)R² are particularly preferably selected from aryl or heteroaryl groups having 6 to 14 aromatic ring atoms, which may be substituted by one or more radicals R⁴.

R³ is preferably selected on each occurrence, identically or differently, from H, D, F, CN, Si(R⁴)₃, a straight-chain alkyl or alkoxy group having 1 to 20 C atoms or a branched or cyclic alkyl or alkoxy group having 3 to 20 C atoms, where the above-mentioned groups may each be substituted by one or more radicals R⁴ and where one or more CH₂ groups in the above-mentioned groups may be replaced by —C≡C—, —R⁴C=CR⁴—, Si(R⁴)₂, C=O, C=NR⁴, —NR⁴—, —O—, —S—, —C(=O)O— or —C(=O)NR⁴—, or an aromatic or heteroaromatic ring system having 5 to 20 aromatic ring atoms, which may in each case be substituted by one or more radicals R⁴, where two or more radicals R³ may be linked to one another and may form a ring.

The groups N(Ar¹)₂ in formula (I) are preferably bonded at positions selected from positions 1, 3, 6 and 8 of the pyrene. Group N(Ar¹)₂ is particularly preferably connected to one another here via groups X bonded at positions 1 and 3 of the pyrene.

Preference is given to the following embodiments of compounds of the formula (I), conforming to formulae (I-1) to (I-5):

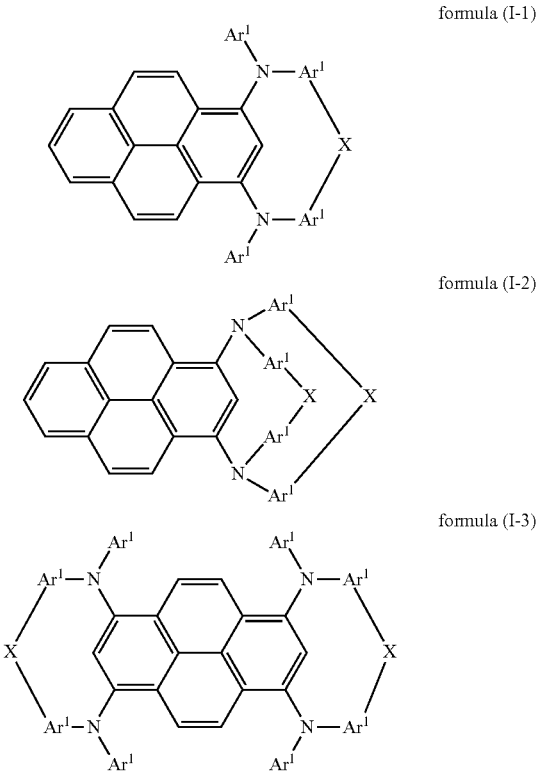

formula (I-1)

formula (I-2)

formula (I-3)

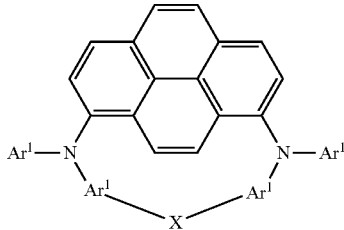

formula (I-4)

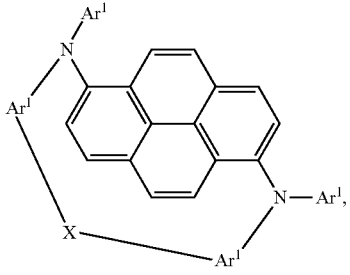

formula (I-5)

where the pyrene group may be substituted by a radical R¹ at any free position, and where the groups are defined as above.

The compound of the formula (I) is preferably selected from compounds of one of the formulae (I-1) to (1-5), where X is selected from the preferred embodiments indicated above, Ar¹ is selected from the preferred embodiments indicated above, R¹ is selected from the embodiments indicated above, R² is selected from the preferred embodiments indicated above, and R³ is selected from the preferred embodiments indicated above.

The compound according to the invention particularly preferably conforms to the formula (I-1).

Furthermore, the compound preferably conforms to the formula (I-1), and

X is selected from C(R²)₂, NR², O and S; and

Ar¹ is selected on each occurrence, identically or differently, from an aromatic ring system having 6 to 12 aromatic ring atoms, preferably a phenyl group, where the aromatic ring system may be substituted by one or more radicals R³; and R¹ is on each occurrence, identically or differently, H, D, F, CN, Si(R⁴)₃, N(Ar¹)₂, a straight-chain alkyl or alkoxy group having 1 to 20 C atoms or a branched or cyclic alkyl or alkoxy group having 3 to 20 C atoms, where the above-mentioned groups may each be substituted by one or more radicals R⁴ and where one or more CH₂ groups in the above-mentioned groups may be replaced by —C≡C—, —R⁴C=CR⁴—, Si(R⁴)₂, C=O, C=NR⁴, —NR⁴—, —O—, —S—, —C(=O)O— or —C(=O)NR⁴—, or an aromatic or heteroaromatic ring system having 5 to 20 aromatic ring atoms, which may in each case be substituted by one or more radicals R⁴, where two or more radicals R¹ may be linked to one another and may form a ring; and R² is on each occurrence, identically or differently, F, CN, a straight-chain alkyl group having 1 to 20 C atoms or a branched or cyclic alkyl group having 3 to 20 C atoms, where the above-mentioned groups may each be substituted by one or more radicals R⁴ and where one or more CH₂ groups in the above-mentioned groups may be replaced by —C≡C—, —R⁴C=CR⁴—, Si(R⁴)₂, C=O, C=NR⁴, —NR⁴—, —O—, —S—, —C(=O)O— or —C(=O)NR⁴—, or an aromatic or heteroaromatic ring system having 5 to 20 aromatic ring atoms, which may in each case be substituted by one or more radicals $R^4$, where two or more radicals $R^2$ may be linked to one another and may form a ring; and $R^3$ is on each occurrence, identically or differently, H, D, F, CN, $Si(R^4)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more $CH_2$ groups in the above-mentioned groups may be replaced by —C≡C—, —$R^4$C=C$R^4$—, $Si(R^4)_2$, C=O, C=$NR^4$, —$NR^4$—, —O—, —S—, —C(=O)O— or —C(=O)$NR^4$—, or an aromatic or heteroaromatic ring system having 5 to 20 aromatic ring atoms, which may in each case be substituted by one or more radicals $R^4$, where two or more radicals $R^3$ may be linked to one another and may form a ring; and $R^4$ is defined as above.

If $Ar^1$ is a phenyl group which is optionally substituted by radicals $R^3$, it is generally preferred that the bond to the group X and to the nitrogen atom on the phenyl group are in the meta position to one another.

It is furthermore generally preferred to combine preferred embodiments of the formula (I) and of the groups of the formula (I) with one another.

Examples of compounds according to the invention are shown in the following table.

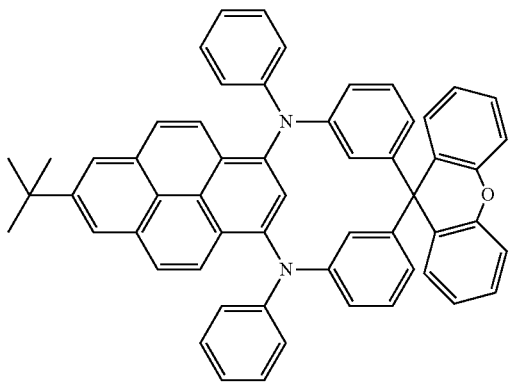 [SMILES: CC(C)(C)c1cc2ccc3c4cc(c5ccc(c1)c2c35)N(c1ccccc1)c1cccc(c1)C1(c2cccc(c2)N4c2ccccc2)c2ccccc2Oc2ccccc21]

(1)

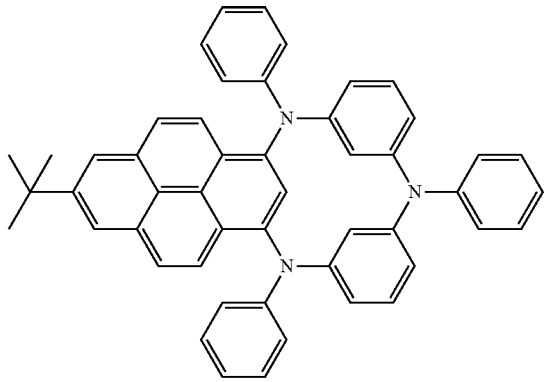 [SMILES: CC(C)(C)c1cc2ccc3c4cc(c5ccc(c1)c2c35)N(c1ccccc1)c1cccc(c1)N(c1ccccc1)c1cccc(c1)N4c1ccccc1]

(2)

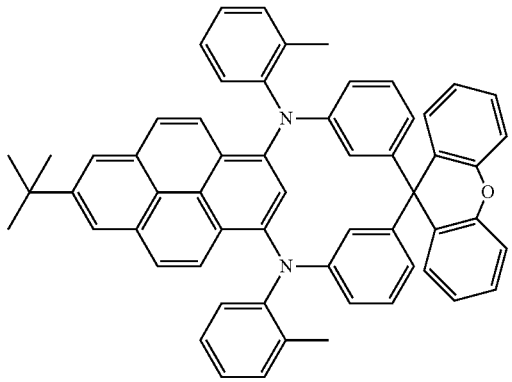 [SMILES: Cc1ccccc1N1c2cccc(c2)C2(c3cccc(c3)N(c3ccccc3C)c3cc1c1ccc4cc(C(C)(C)C)cc5ccc3c1c45)c1ccccc1Oc1ccccc12]

(3)

-continued
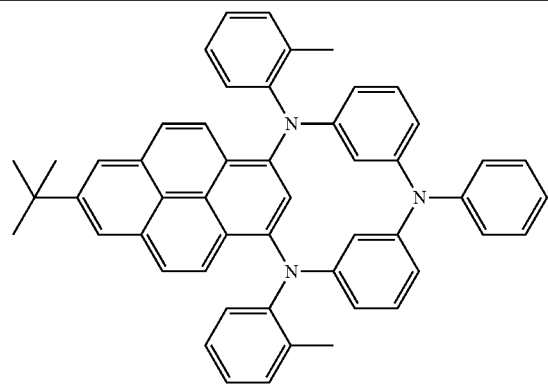
(4)
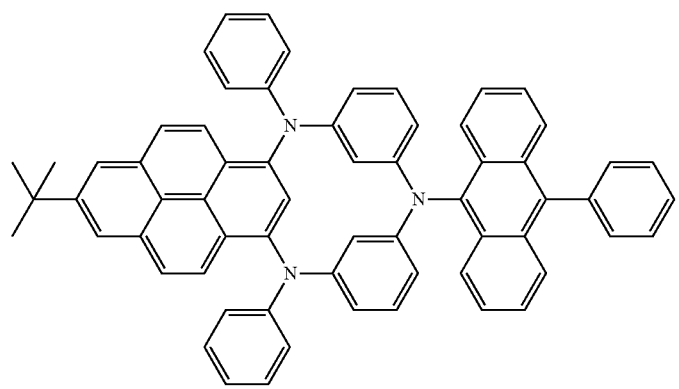 [SMILES: CC(C)(C)c1cc2ccc3c4cc(c5ccc(c1)c2c35)N(c1ccccc1)c1cccc(c1)N(c1c2ccccc2c(-c2ccccc2)c2ccccc12)c1cccc(c1)N4c1ccccc1]
(5)
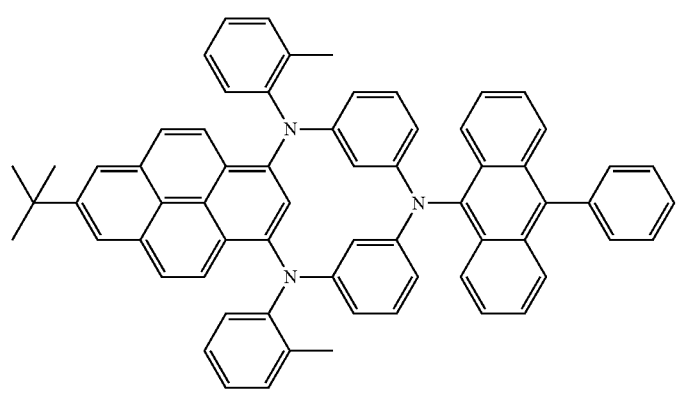 [SMILES: Cc1ccccc1N1c2cccc(c2)N(c2c3ccccc3c(-c3ccccc3)c3ccccc23)c2cccc(c2)N(c2ccccc2C)c2cc1c1ccc3cc(C(C)(C)C)cc4ccc2c1c34]
(6)
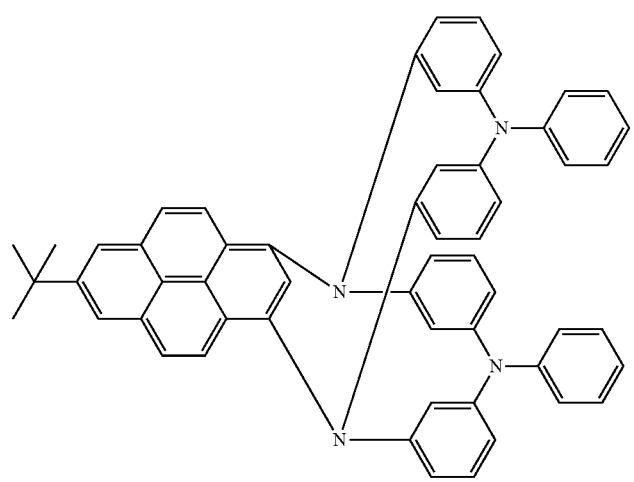 [SMILES: CC(C)(C)c1cc2ccc3c4cc(c5ccc(c1)c2c35)N1c2cccc(c2)N(c2ccccc2)c2cccc(c2)N4c2cccc(c2)N(c2ccccc2)c2cccc1c2]
(7)

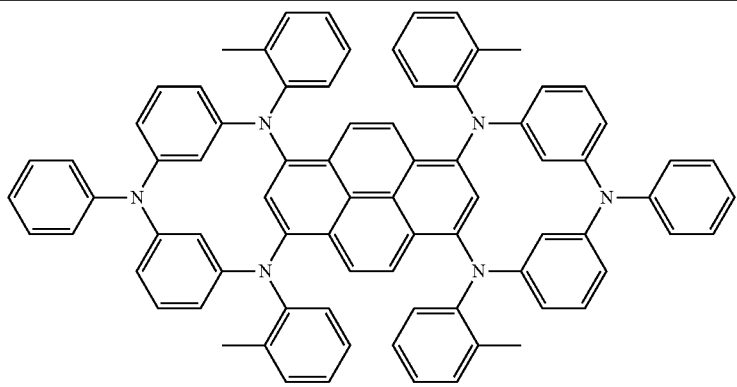
(8)
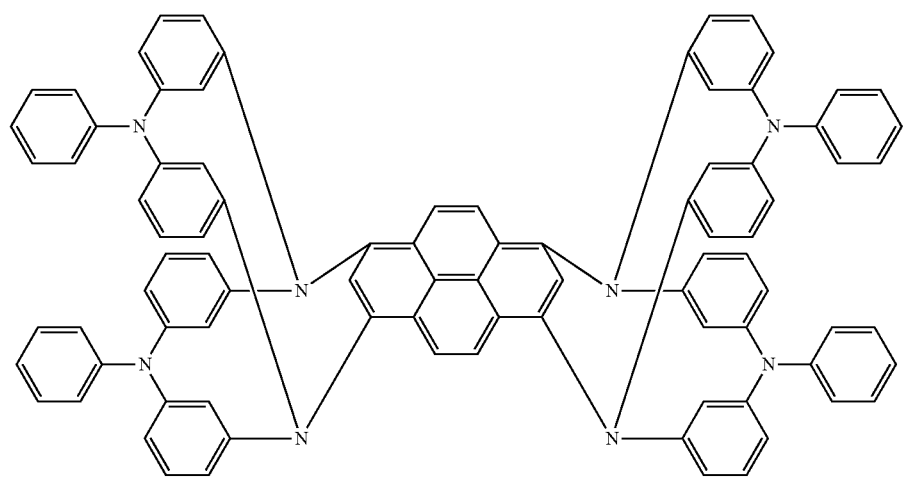 [SMILES: c1ccc(N2c3cccc(c3)N3c4cccc(c4)N(c4ccccc4)c4cccc(c4)N(c4cccc2c4)c2cc3c3ccc4c5cc(c6ccc2c3c46)N2c3cccc(c3)N(c3ccccc3)c3cccc(c3)N5c3cccc(c3)N(c3ccccc3)c3cccc2c3)cc1]
(9)
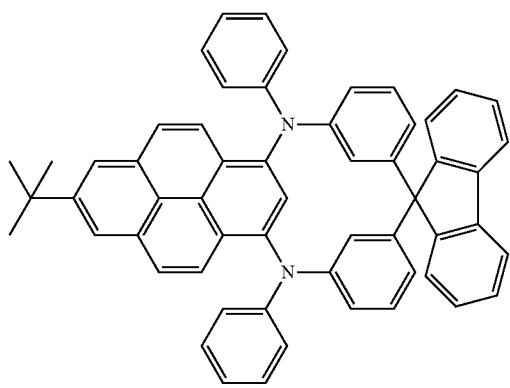 [SMILES: CC(C)(C)c1cc2ccc3c4cc(c5ccc(c1)c2c35)N(c1ccccc1)c1cccc(c1)C1(c2cccc(c2)N4c2ccccc2)c2ccccc2-c2ccccc21]
(10)
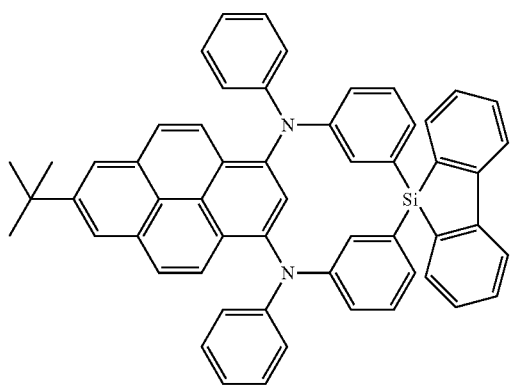
(11)

(12)
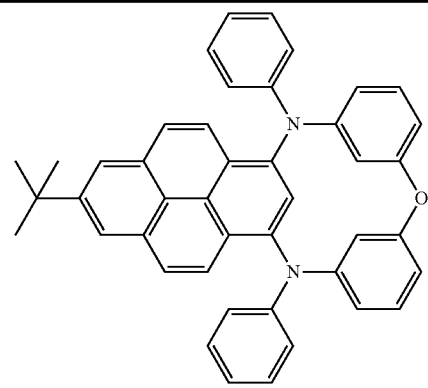
(13)
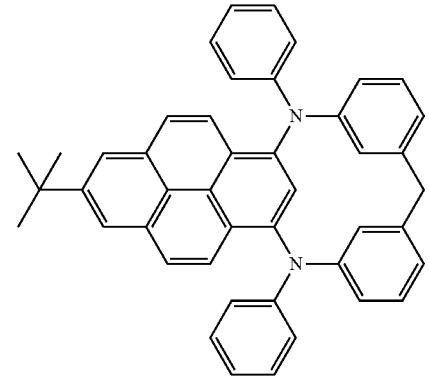 [SMILES: CC(C)(C)c1cc2ccc3c4cc(c5ccc(c1)c2c35)N(c1ccccc1)c1cccc(c1)Cc1cccc(c1)N4c1ccccc1]
(14)
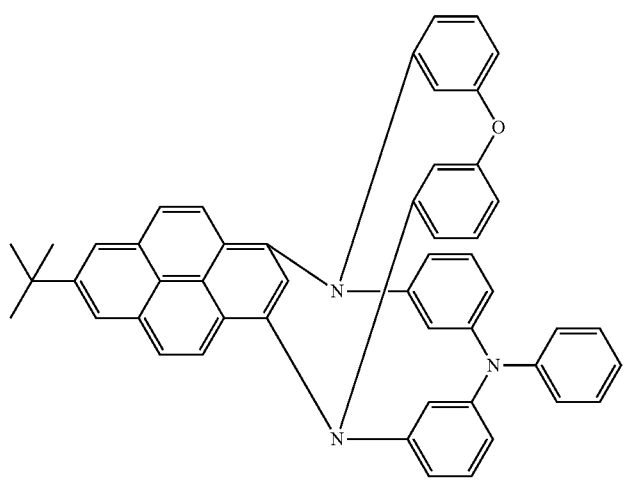 [SMILES: CC(C)(C)c1cc2ccc3c4cc(c5ccc(c1)c2c35)N1c2cccc(c2)Oc2cccc(c2)N4c2cccc(c2)N(c2ccccc2)c2cccc1c2]
(15)
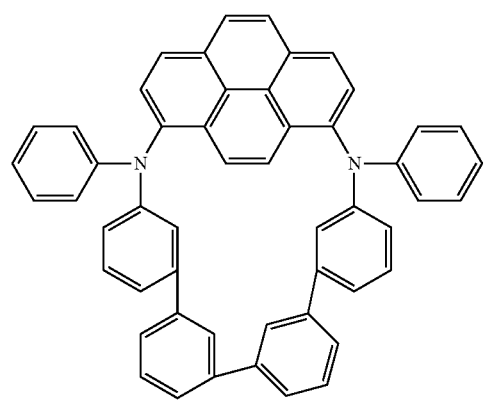 [SMILES: c1ccc(-n2c3cccc(c3)c3cccc(c3)c3cccc(c3)c3cccc(c3)n(-c3ccccc3)c3ccc4ccc5ccc2c2ccc3c4c52)cc1]

-continued
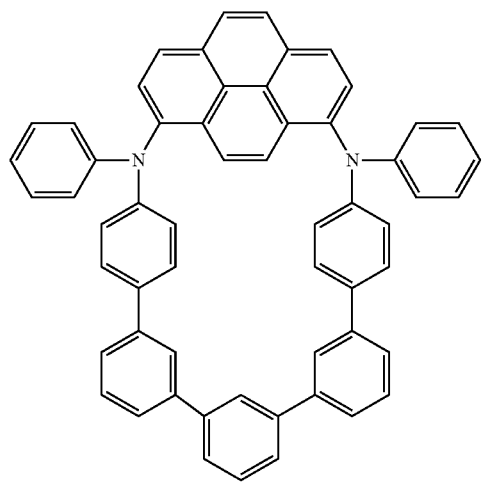 [SMILES: c1ccc(N2c3ccc(cc3)-c3cccc(c3)-c3cccc(c3)-c3cccc(c3)-c3ccc(cc3)N(c3ccccc3)c3ccc4ccc5ccc2c2ccc3c4c52)cc1]
(16)
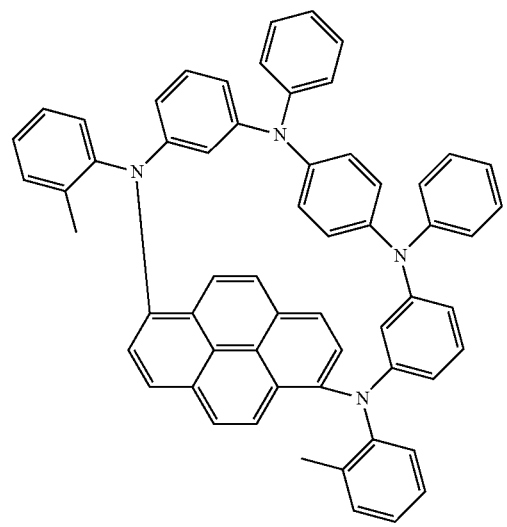 [SMILES: Cc1ccccc1N1c2cccc(c2)N(c2ccccc2)c2ccc(cc2)N(c2ccccc2)c2cccc(c2)N(c2ccccc2C)c2ccc3ccc4c1ccc1ccc2c3c14]
(17)
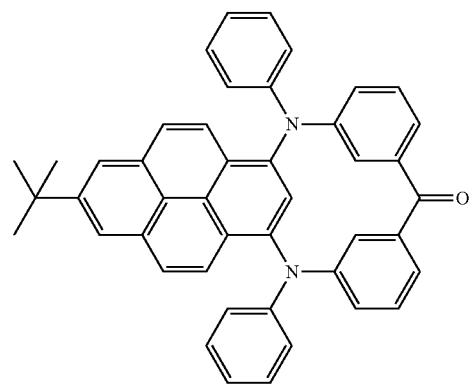 [SMILES: CC(C)(C)c1cc2ccc3c4cc(c5ccc(c1)c2c35)N(c1ccccc1)c1cccc(c1)C(=O)c1cccc(c1)N4c1ccccc1]
(18)

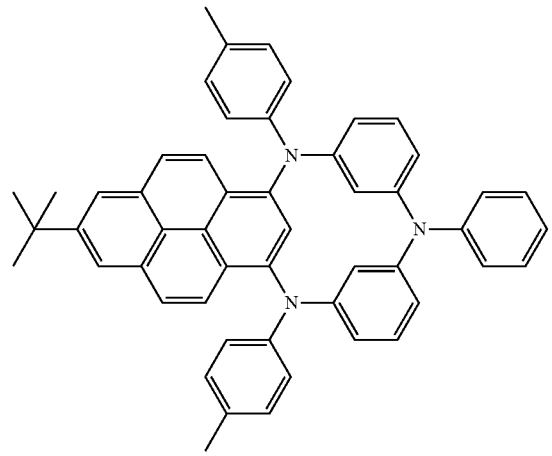
(19)
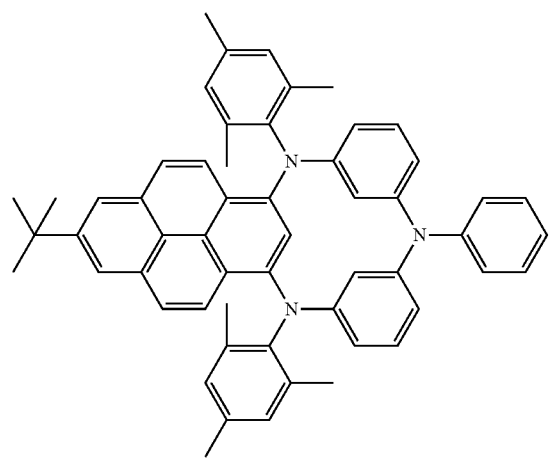 [SMILES: Cc1cc(C)c(N2c3cccc(c3)N(c3ccccc3)c3cccc(c3)N(c3c(C)cc(C)cc3C)c3cc2c2ccc4cc(C(C)(C)C)cc5ccc3c2c45)c(C)c1]
(20)
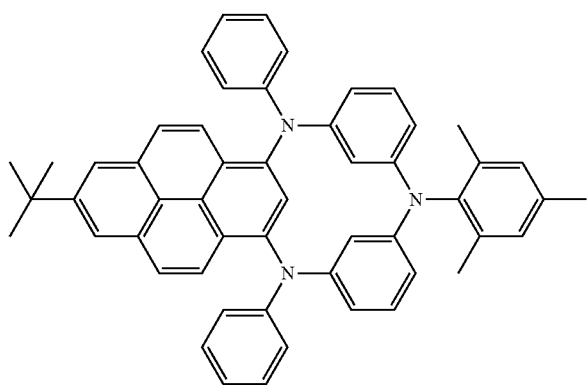 [SMILES: Cc1cc(C)c(N2c3cccc(c3)N(c3ccccc3)c3cc(c4ccc5cc(C(C)(C)C)cc6ccc3c4c65)N(c3ccccc3)c3cccc2c3)c(C)c1]
(21)

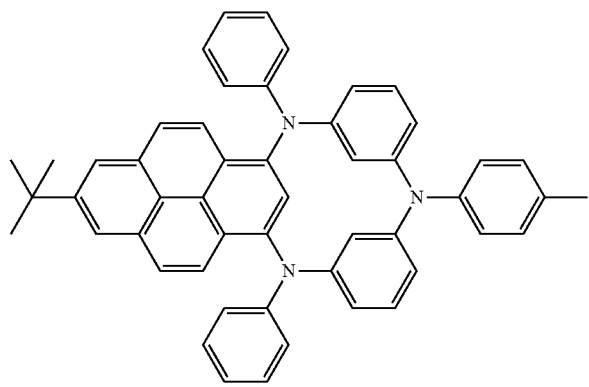 [SMILES: Cc1ccc(N2c3cccc(c3)N(c3ccccc3)c3cc(c4ccc5cc(C(C)(C)C)cc6ccc3c4c65)N(c3ccccc3)c3cccc2c3)cc1]
(22)
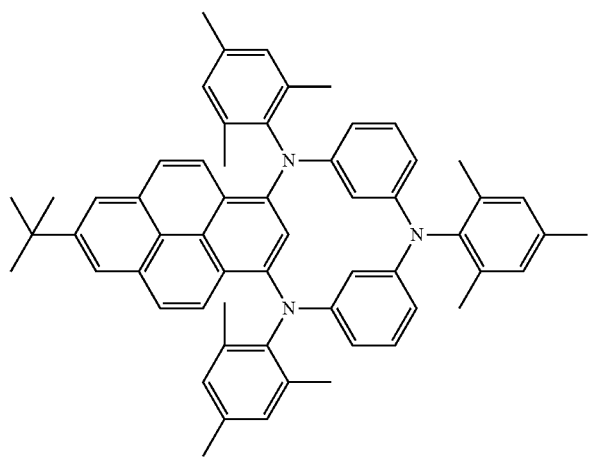 [SMILES: Cc1cc(C)c(N2c3cccc(c3)N(c3c(C)cc(C)cc3C)c3cc(c4ccc5cc(C(C)(C)C)cc6ccc3c4c65)N(c3c(C)cc(C)cc3C)c3cccc2c3)c(C)c1]
(23)
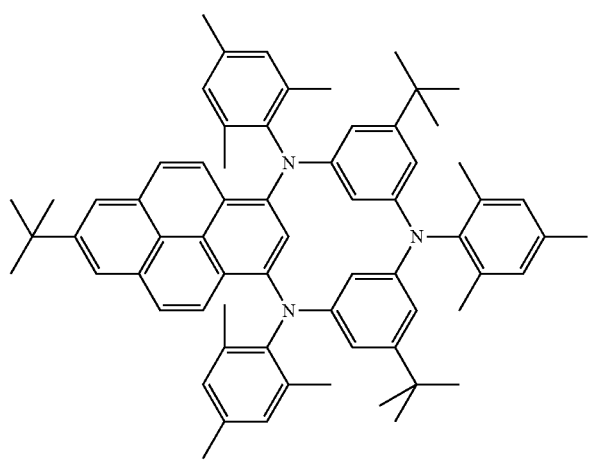 [SMILES: Cc1cc(C)c(N2c3cc(cc(C(C)(C)C)c3)N(c3c(C)cc(C)cc3C)c3cc(c4ccc5cc(C(C)(C)C)cc6ccc3c4c65)N(c3c(C)cc(C)cc3C)c3cc2cc(C(C)(C)C)c3)c(C)c1]
(24)

(25)
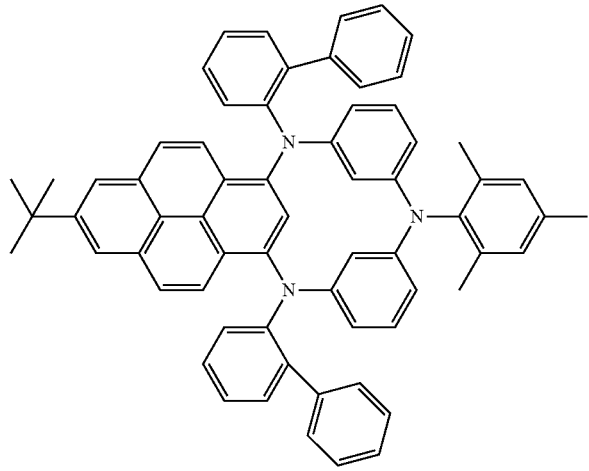 [SMILES: Cc1cc(C)c(N2c3cccc(c3)N(c3ccccc3-c3ccccc3)c3cc(c4ccc5cc(C(C)(C)C)cc6ccc3c4c65)N(c3ccccc3-c3ccccc3)c3cccc2c3)c(C)c1]
(26)
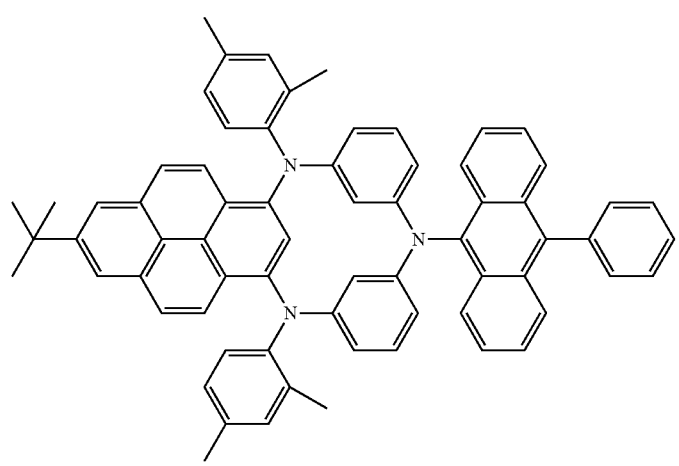 [SMILES: Cc1ccc(N2c3cccc(c3)N(c3c4ccccc4c(-c4ccccc4)c4ccccc34)c3cccc(c3)N(c3ccc(C)cc3C)c3cc2c2ccc4cc(C(C)(C)C)cc5ccc3c2c45)c(C)c1]
(27)
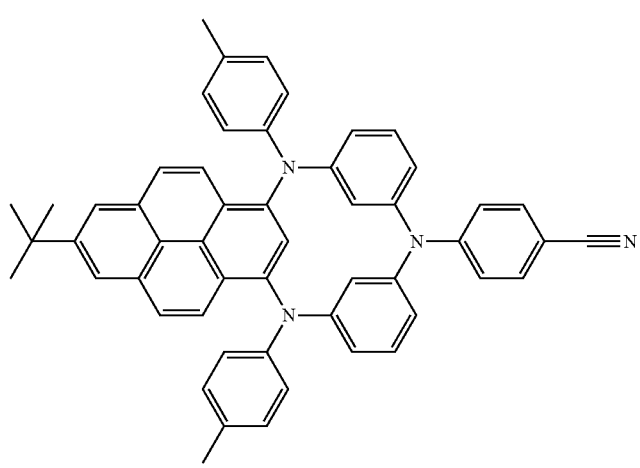 [SMILES: Cc1ccc(N2c3cccc(c3)N(c3ccc(C#N)cc3)c3cccc(c3)N(c3ccc(C)cc3)c3cc2c2ccc4cc(C(C)(C)C)cc5ccc3c2c45)cc1]

(28)
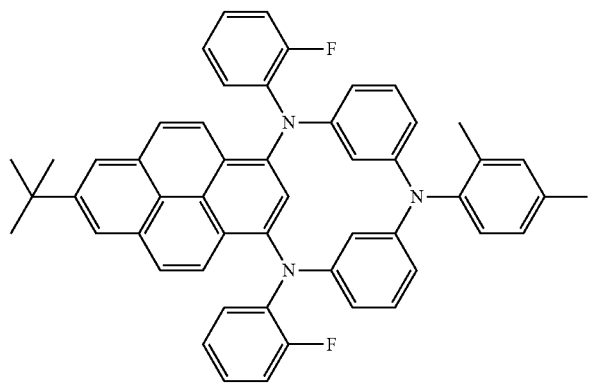 [SMILES: Cc1ccc(N2c3cccc(c3)N(c3ccccc3F)c3cc(c4ccc5cc(C(C)(C)C)cc6ccc3c4c65)N(c3ccccc3F)c3cccc2c3)c(C)c1]
(29)
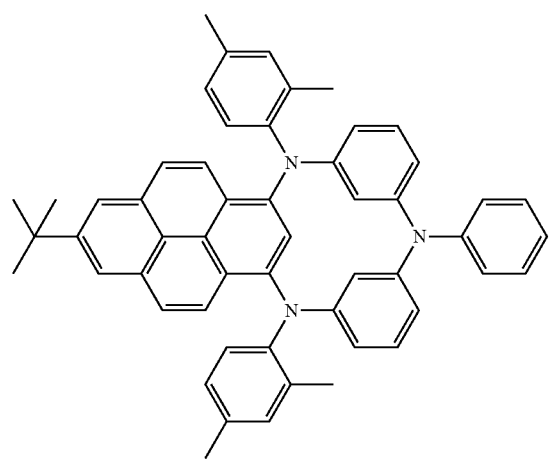 [SMILES: Cc1ccc(N2c3cccc(c3)N(c3ccccc3)c3cccc(c3)N(c3ccc(C)cc3C)c3cc2c2ccc4cc(C(C)(C)C)cc5ccc3c2c45)c(C)c1]
(30)
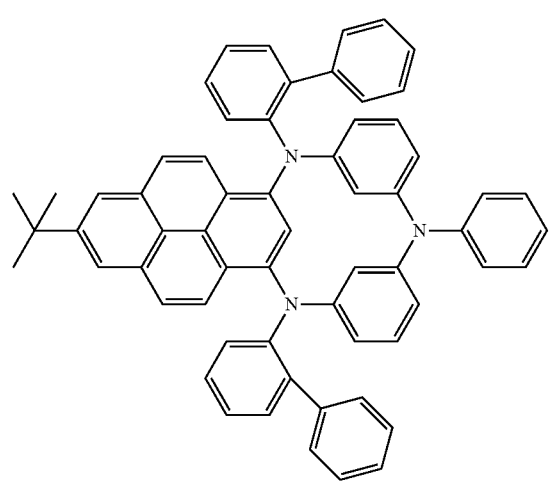 [SMILES: CC(C)(C)c1cc2ccc3c4cc(c5ccc(c1)c2c35)N(c1ccccc1-c1ccccc1)c1cccc(c1)N(c1ccccc1)c1cccc(c1)N4c1ccccc1-c1ccccc1]

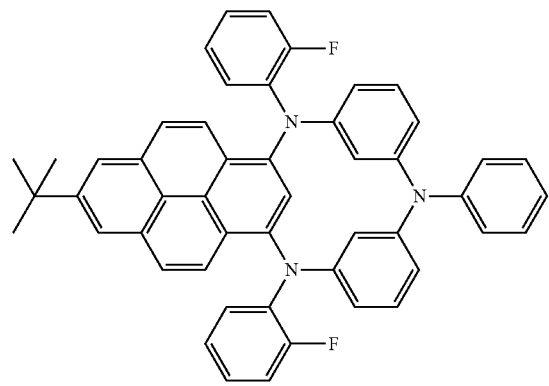 [SMILES: CC(C)(C)c1cc2ccc3c4cc(c5ccc(c1)c2c35)N(c1ccccc1F)c1cccc(c1)N(c1ccccc1)c1cccc(c1)N4c1ccccc1F]
(31)
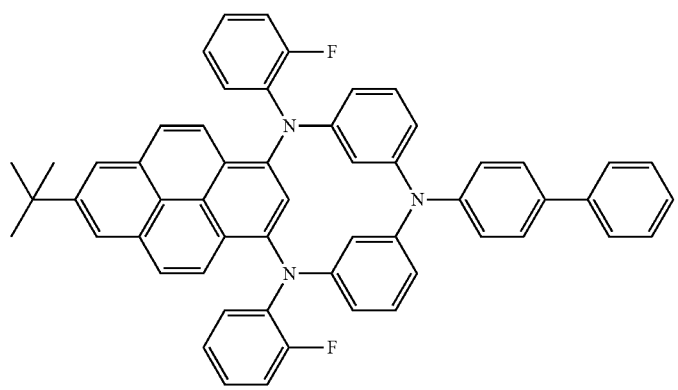 [SMILES: CC(C)(C)c1cc2ccc3c4cc(c5ccc(c1)c2c35)N(c1ccccc1F)c1cccc(c1)N(c1ccc(-c2ccccc2)cc1)c1cccc(c1)N4c1ccccc1F]
(32)
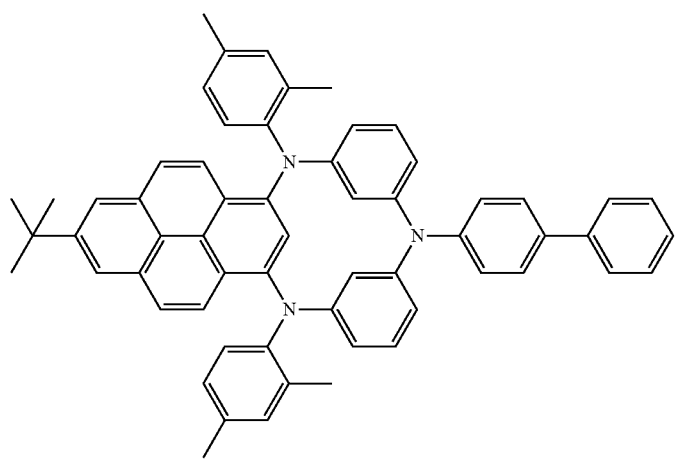 [SMILES: Cc1ccc(N2c3cccc(c3)N(c3ccc(-c4ccccc4)cc3)c3cccc(c3)N(c3ccc(C)cc3C)c3cc2c2ccc4cc(C(C)(C)C)cc5ccc3c2c45)c(C)c1]
(33)
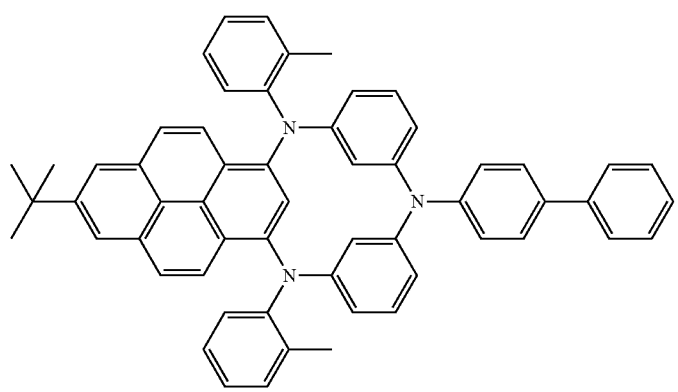
(34)

-continued
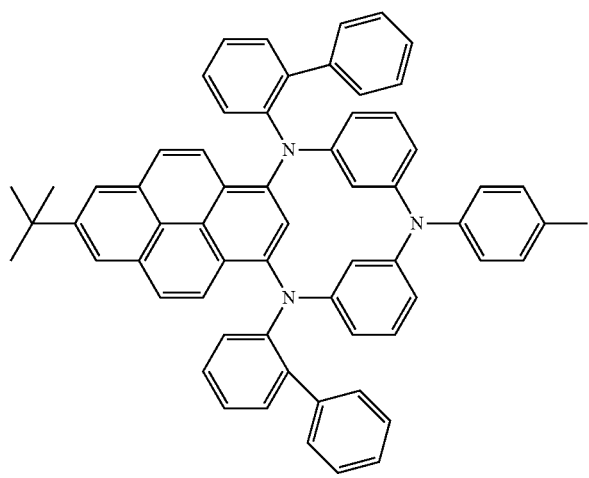 [SMILES: Cc1ccc(N2c3cccc(c3)N(c3ccccc3-c3ccccc3)c3cc(c4ccc5cc(C(C)(C)C)cc6ccc3c4c65)N(c3ccccc3-c3ccccc3)c3cccc2c3)cc1]
(35)
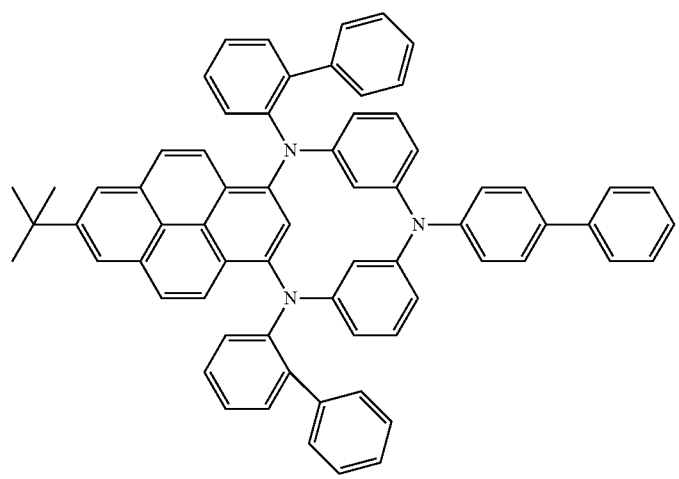 [SMILES: CC(C)(C)c1cc2ccc3c4cc(c5ccc(c1)c2c35)N(c1ccccc1-c1ccccc1)c1cccc(c1)N(c1ccc(-c2ccccc2)cc1)c1cccc(c1)N4c1ccccc1-c1ccccc1]
(36)
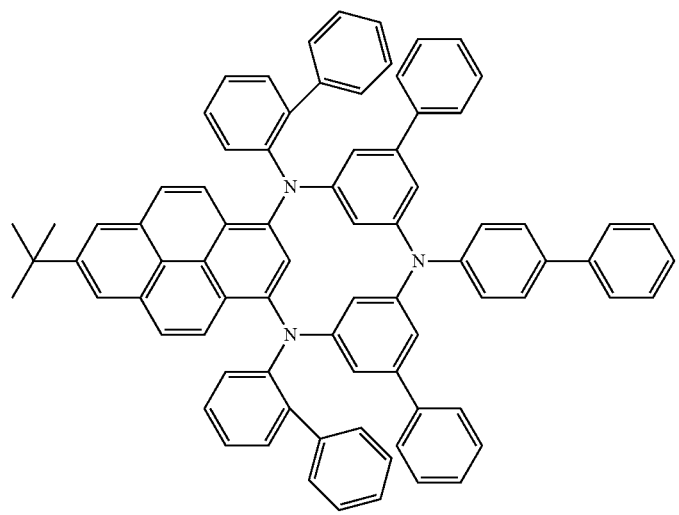 [SMILES: CC(C)(C)c1cc2ccc3c4cc(c5ccc(c1)c2c35)N(c1ccccc1-c1ccccc1)c1cc(-c2ccccc2)cc(c1)N(c1ccc(-c2ccccc2)cc1)c1cc(-c2ccccc2)cc(c1)N4c1ccccc1-c1ccccc1]
(37)

-continued
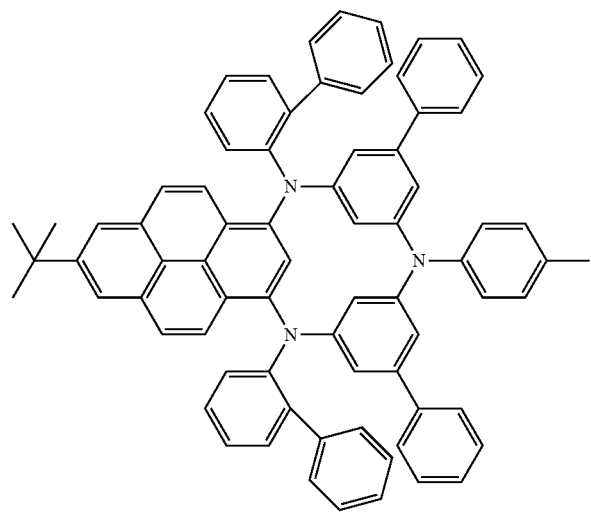 [SMILES: Cc1ccc(N2c3cc(-c4ccccc4)cc(c3)N(c3ccccc3-c3ccccc3)c3cc(c4ccc5cc(C(C)(C)C)cc6ccc3c4c65)N(c3ccccc3-c3ccccc3)c3cc(-c4ccccc4)cc2c3)cc1]
(38)
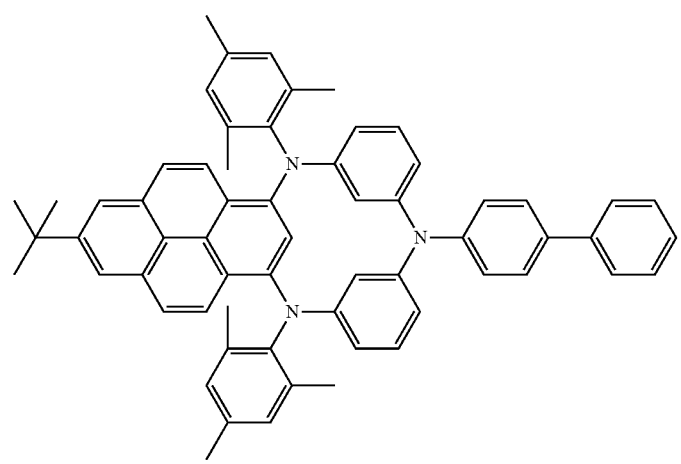 [SMILES: Cc1cc(C)c(N2c3cccc(c3)N(c3ccc(-c4ccccc4)cc3)c3cccc(c3)N(c3c(C)cc(C)cc3C)c3cc2c2ccc4cc(C(C)(C)C)cc5ccc3c2c45)c(C)c1]
(39)
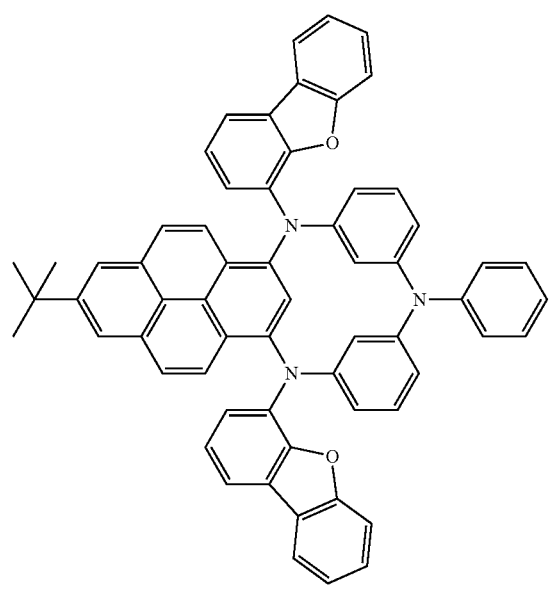 [SMILES: CC(C)(C)c1cc2ccc3c4cc(c5ccc(c1)c2c35)N(c1cccc2c1oc1ccccc12)c1cccc(c1)N(c1ccccc1)c1cccc(c1)N4c1cccc2c1oc1ccccc12]
(40)

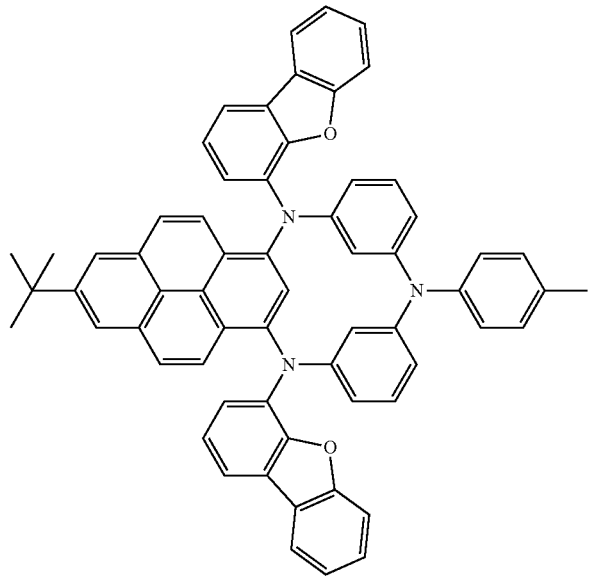
(41)
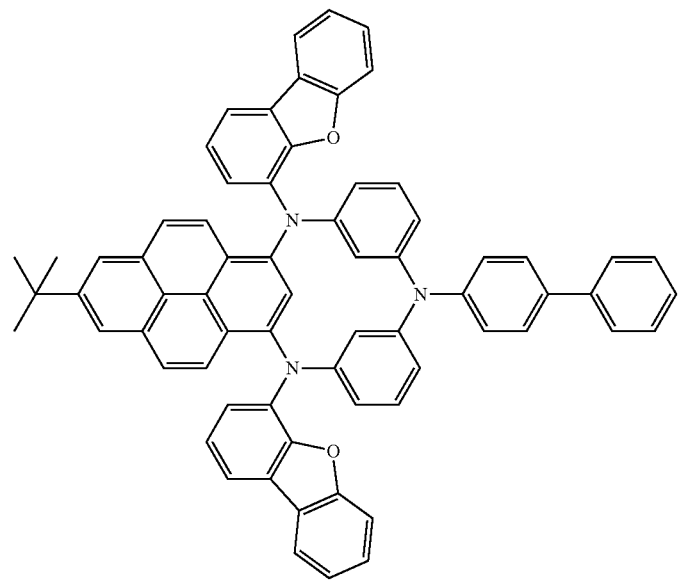 [SMILES: CC(C)(C)c1cc2ccc3c4cc(c5ccc(c1)c2c35)N(c1cccc2c1oc1ccccc12)c1cccc(c1)N(c1ccc(-c2ccccc2)cc1)c1cccc(c1)N4c1cccc2c1oc1ccccc12]
(42)

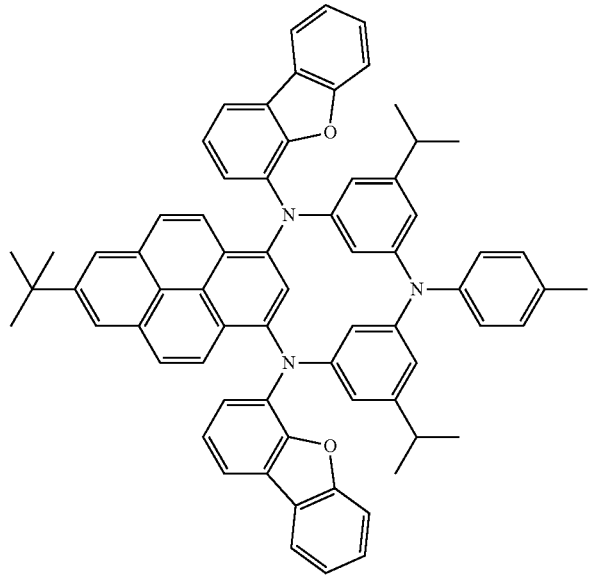 [SMILES: Cc1ccc(N2c3cc(C(C)C)cc(c3)N(c3cccc4c3oc3ccccc34)c3cc(c4ccc5cc(C(C)(C)C)cc6ccc3c4c65)N(c3cccc4c3oc3ccccc34)c3cc(C(C)C)cc2c3)cc1]
(43)
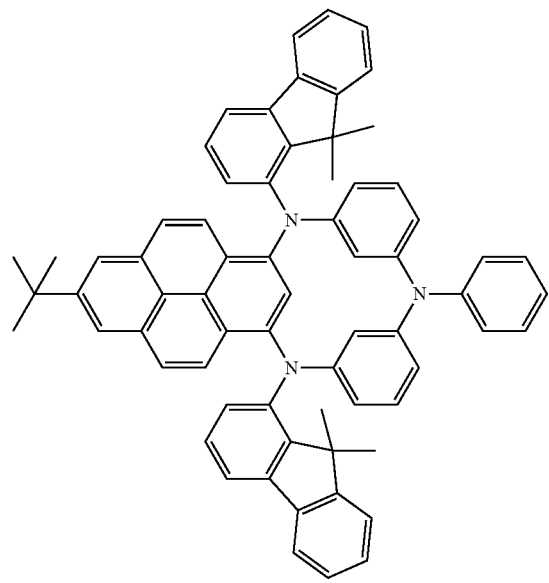 [SMILES: CC(C)(C)c1cc2ccc3c4cc(c5ccc(c1)c2c35)N(c1cccc2c1C(C)(C)c1ccccc1-2)c1cccc(c1)N(c1ccccc1)c1cccc(c1)N4c1cccc2c1C(C)(C)c1ccccc1-2]
(44)

-continued
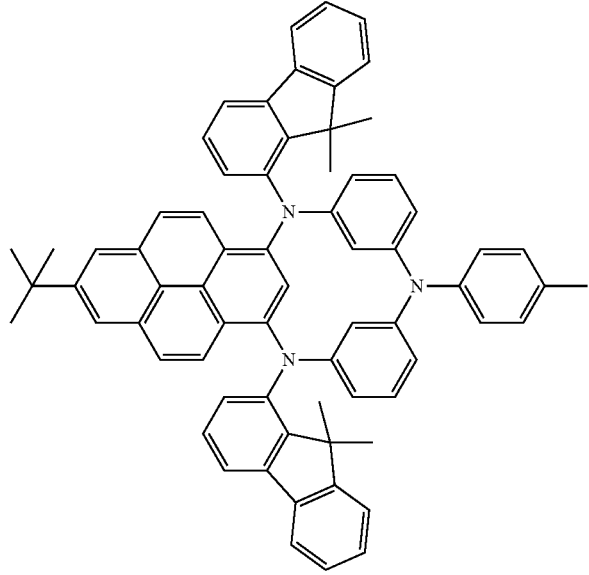
(45)
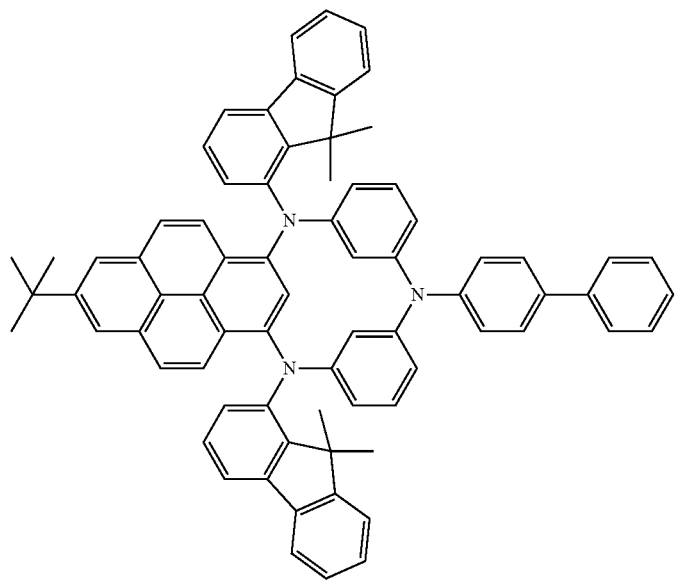 [SMILES: CC(C)(C)c1cc2ccc3c4cc(c5ccc(c1)c2c35)N(c1cccc2c1C(C)(C)c1ccccc1-2)c1cccc(c1)N(c1ccc(-c2ccccc2)cc1)c1cccc(c1)N4c1cccc2c1C(C)(C)c1ccccc1-2]
(46)
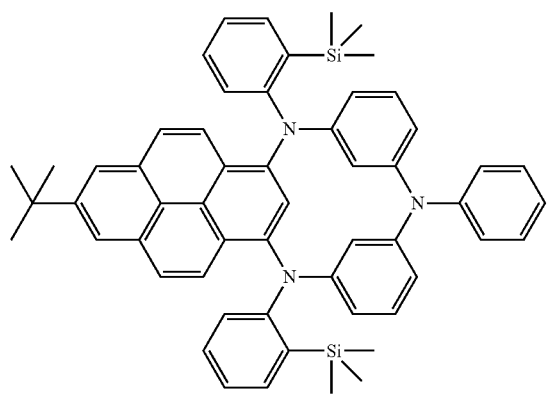 [SMILES: CC(C)(C)c1cc2ccc3c4cc(c5ccc(c1)c2c35)N(c1ccccc1[Si](C)(C)C)c1cccc(c1)N(c1ccccc1)c1cccc(c1)N4c1ccccc1[Si](C)(C)C]
(47)

-continued
(48)
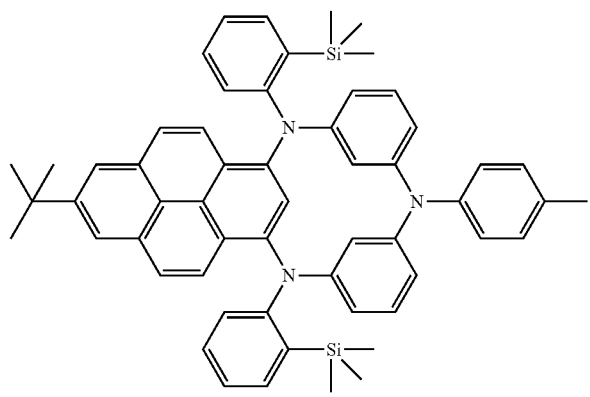 [SMILES: Cc1ccc(N2c3cccc(c3)N(c3ccccc3[Si](C)(C)C)c3cc(c4ccc5cc(C(C)(C)C)cc6ccc3c4c65)N(c3ccccc3[Si](C)(C)C)c3cccc2c3)cc1]
(49)
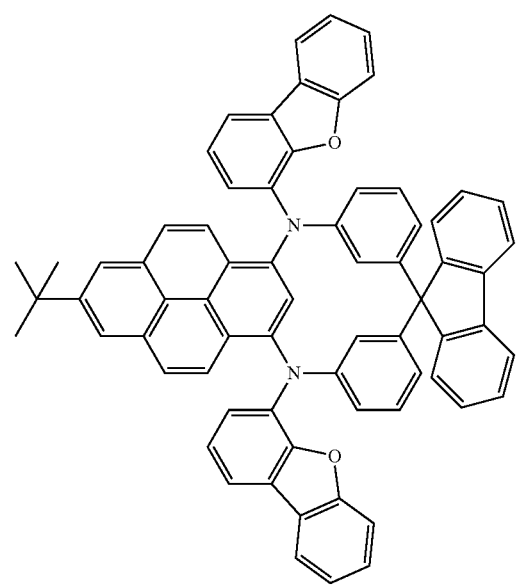 [SMILES: CC(C)(C)c1cc2ccc3c4cc(c5ccc(c1)c2c35)N(c1cccc2c1oc1ccccc12)c1cccc(c1)C1(c2cccc(c2)N4c2cccc3c2oc2ccccc23)c2ccccc2-c2ccccc21]
(50)
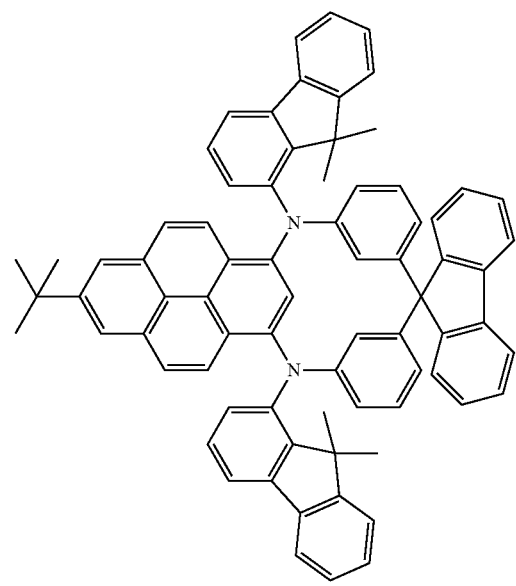 [SMILES: CC(C)(C)c1cc2ccc3c4cc(c5ccc(c1)c2c35)N(c1cccc2c1C(C)(C)c1ccccc1-2)c1cccc(c1)C1(c2cccc(c2)N4c2cccc3c2C(C)(C)c2ccccc2-3)c2ccccc2-c2ccccc21]

(51)
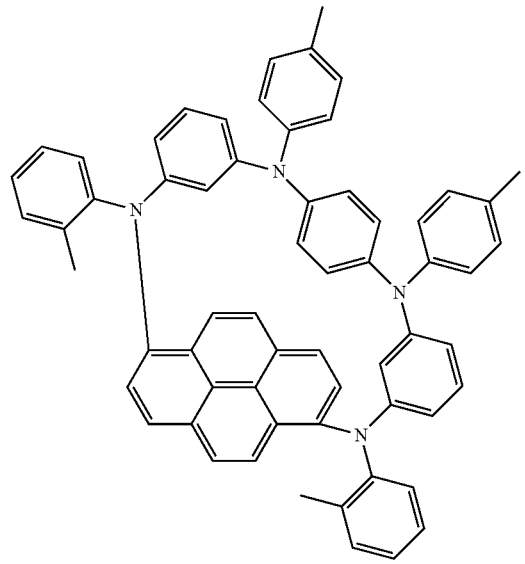 [SMILES: Cc1ccc(N2c3ccc(cc3)N(c3ccc(C)cc3)c3cccc(c3)N(c3ccccc3C)c3ccc4ccc5c(ccc6ccc3c4c65)N(c3ccccc3C)c3cccc2c3)cc1]
(52)
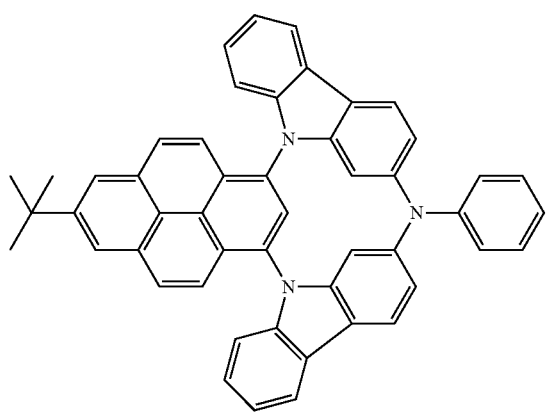 [SMILES: CC(C)(C)c1cc2ccc3c4c(ccc(c1)c24)c1cc3n2c3ccccc3c3ccc(cc32)n(-c2ccccc2)c2ccc3c4ccccc4n1c3c2]
(53)
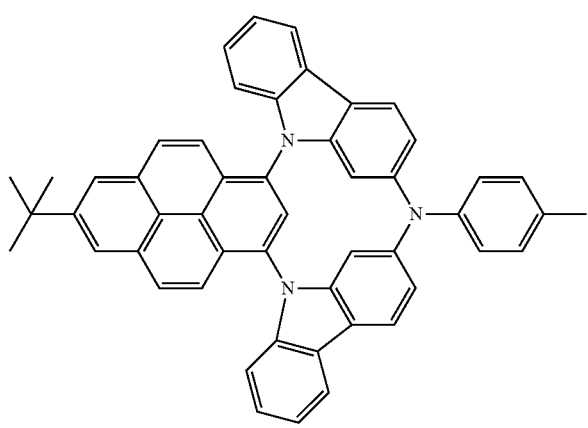 [SMILES: Cc1ccc(-n2c3ccc4c5ccccc5n(c4c3)c3cc(c4ccc5cc(C(C)(C)C)cc6ccc3c4c65)n3c4ccccc4c4ccc2cc43)cc1]

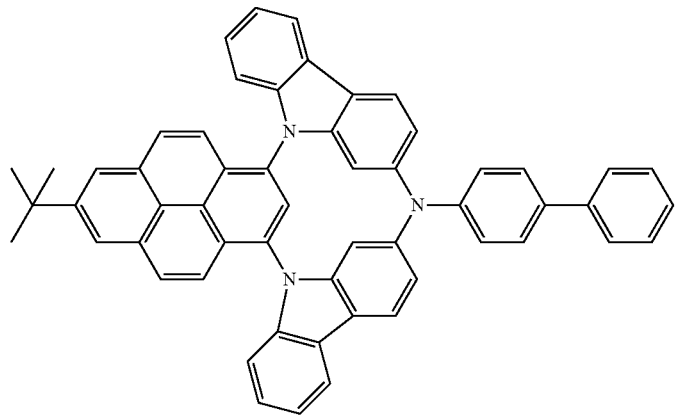 [SMILES: CC(C)(C)c1cc2ccc3c4c(ccc(c1)c24)c1cc3n2c3ccccc3c3ccc(cc32)n(-c2ccc(-c3ccccc3)cc2)c2ccc3c4ccccc4n1c3c2]
(54)
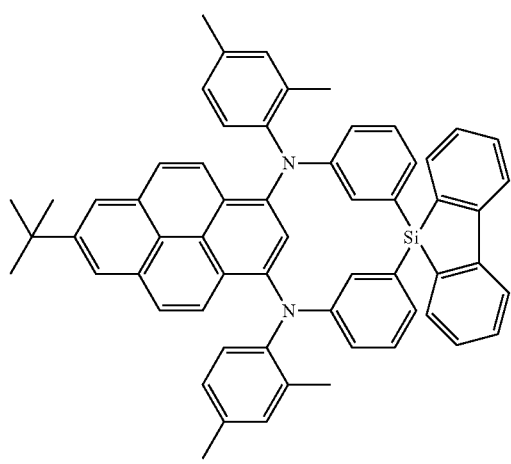 [SMILES: Cc1ccc(N2c3cccc(c3)[Si]3(c4cccc(c4)N(c4ccc(C)cc4C)c4cc2c2ccc5cc(C(C)(C)C)cc6ccc4c2c56)c2ccccc2-c2ccccc23)c(C)c1]
(55)
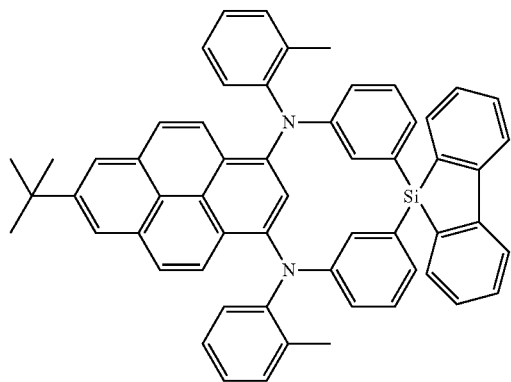 [SMILES: Cc1ccccc1N1c2cccc(c2)[Si]2(c3cccc(c3)N(c3ccccc3C)c3cc1c1ccc4cc(C(C)(C)C)cc5ccc3c1c45)c1ccccc1-c1ccccc12]
(56)

(57)
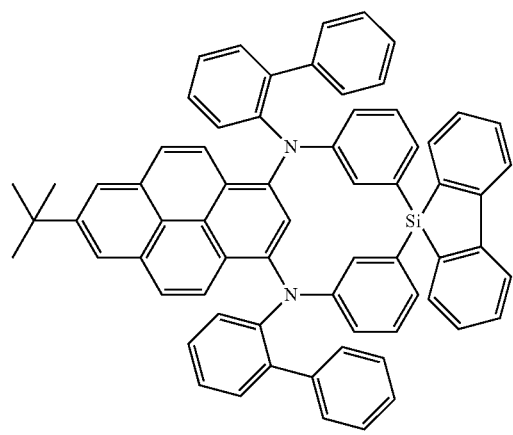 [SMILES: CC(C)(C)c1cc2ccc3c4cc(c5ccc(c1)c2c35)N(c1ccccc1-c1ccccc1)c1cccc(c1)[Si]1(c2cccc(c2)N4c2ccccc2-c2ccccc2)c2ccccc2-c2ccccc21]
(58)
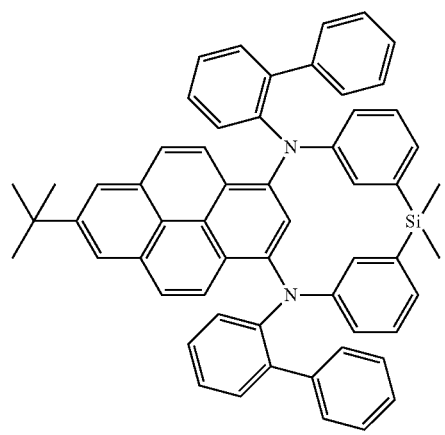 [SMILES: CC(C)(C)c1cc2ccc3c4cc(c5ccc(c1)c2c35)N(c1ccccc1-c1ccccc1)c1cccc(c1)[Si](C)(C)c1cccc(c1)N4c1ccccc1-c1ccccc1]
(59)
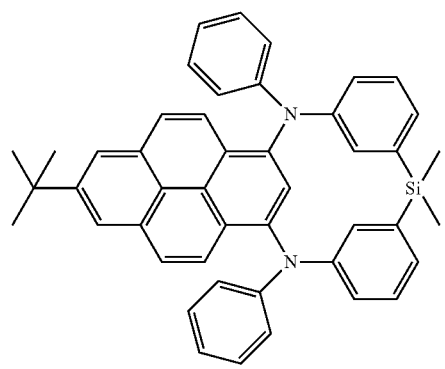
(60)
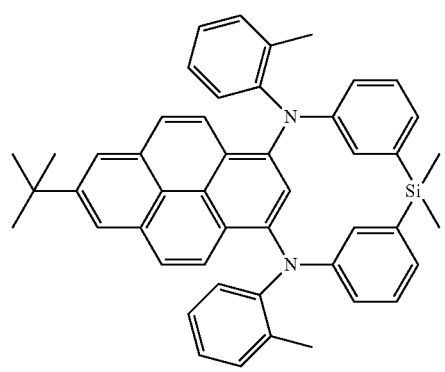

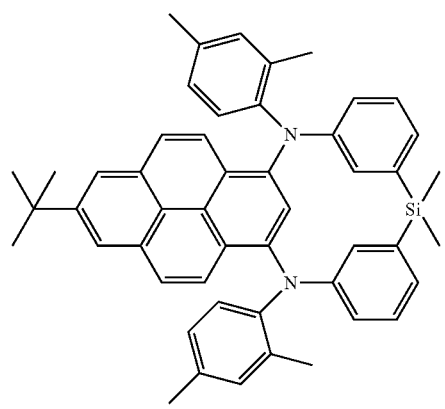 [SMILES: Cc1ccc(N2c3cccc(c3)[Si](C)(C)c3cccc(c3)N(c3ccc(C)cc3C)c3cc2c2ccc4cc(C(C)(C)C)cc5ccc3c2c45)c(C)c1]
(61)
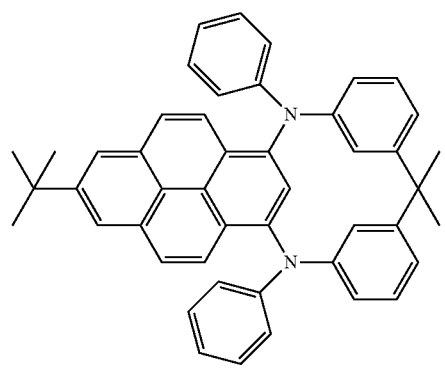 [SMILES: CC(C)(C)c1cc2ccc3c4cc(c5ccc(c1)c2c35)N(c1ccccc1)c1cccc(c1)C(C)(C)c1cccc(c1)N4c1ccccc1]
(62)
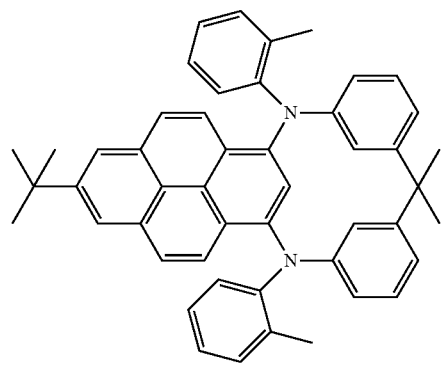 [SMILES: Cc1ccccc1N1c2cccc(c2)C(C)(C)c2cccc(c2)N(c2ccccc2C)c2cc1c1ccc3cc(C(C)(C)C)cc4ccc2c1c34]
(63)
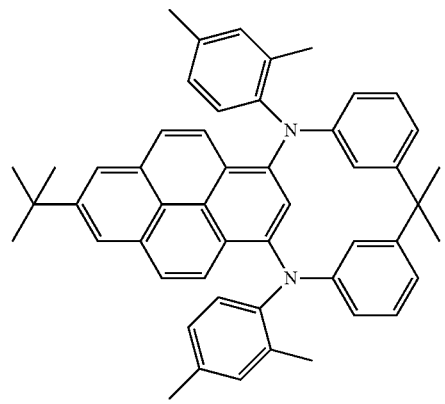 [SMILES: Cc1ccc(N2c3cccc(c3)C(C)(C)c3cccc(c3)N(c3ccc(C)cc3C)c3cc2c2ccc4cc(C(C)(C)C)cc5ccc3c2c45)c(C)c1]
(64)

(65)
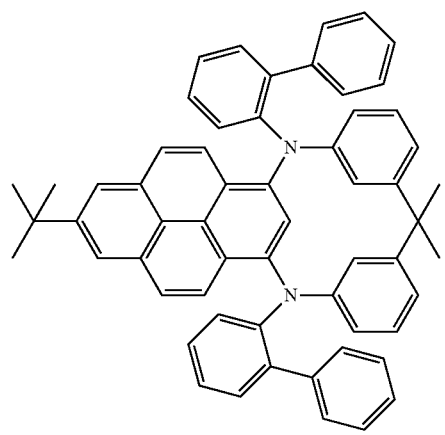 [SMILES: CC(C)(C)c1cc2ccc3c4cc(c5ccc(c1)c2c35)N(c1ccccc1-c1ccccc1)c1cccc(c1)C(C)(C)c1cccc(c1)N4c1ccccc1-c1ccccc1]
(66)
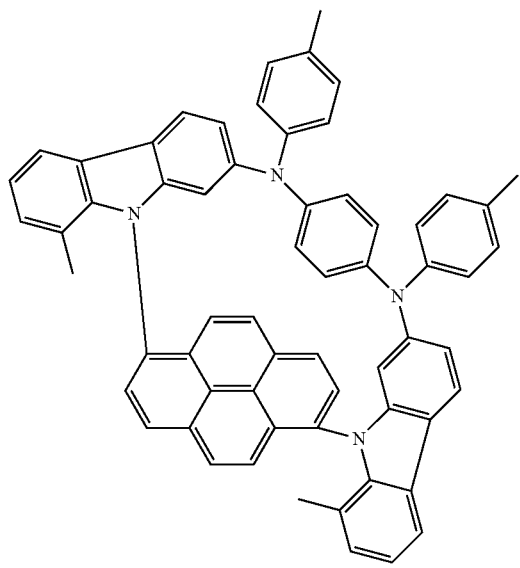 [SMILES: Cc1ccc(-n2c3ccc(cc3)n(-c3ccc(C)cc3)c3ccc4c5cccc(C)c5n(c4c3)c3ccc4ccc5c6c(ccc3c46)ccc5n3c4cc2ccc4c2cccc(C)c23)cc1]
(67)
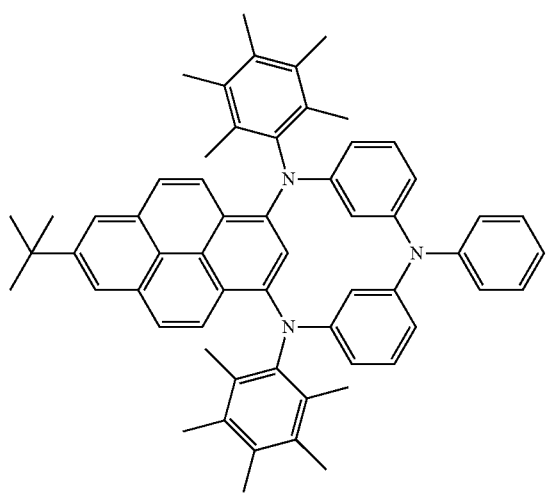 [SMILES: Cc1c(C)c(C)c(N2c3cccc(c3)N(c3ccccc3)c3cccc(c3)N(c3c(C)c(C)c(C)c(C)c3C)c3cc2c2ccc4cc(C(C)(C)C)cc5ccc3c2c45)c(C)c1C]

(68)
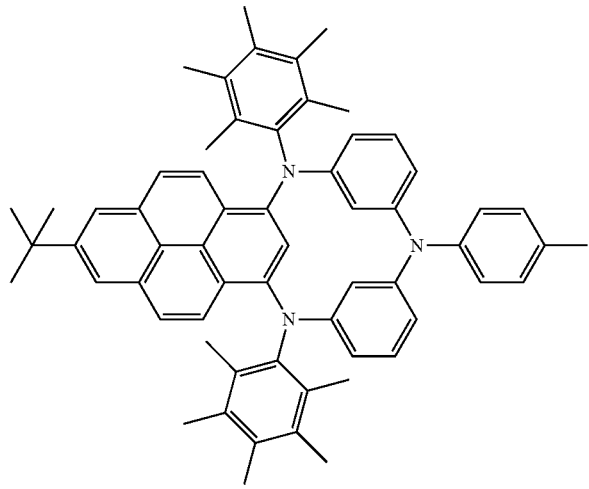 [SMILES: Cc1ccc(N2c3cccc(c3)N(c3c(C)c(C)c(C)c(C)c3C)c3cc(c4ccc5cc(C(C)(C)C)cc6ccc3c4c65)N(c3c(C)c(C)c(C)c(C)c3C)c3cccc2c3)cc1]
(69)
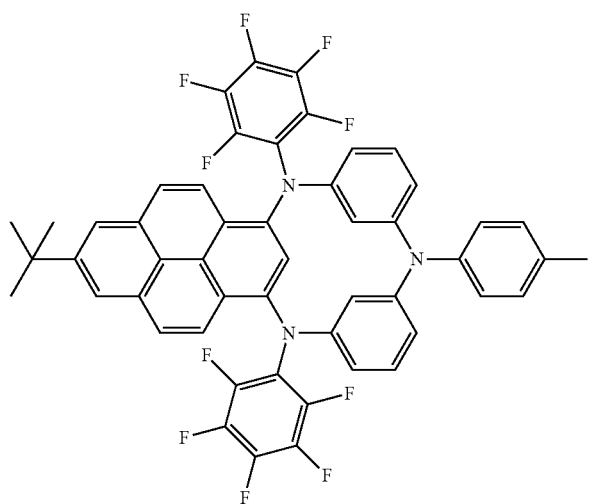 [SMILES: Cc1ccc(N2c3cccc(c3)N(c3c(F)c(F)c(F)c(F)c3F)c3cc(c4ccc5cc(C(C)(C)C)cc6ccc3c4c65)N(c3c(F)c(F)c(F)c(F)c3F)c3cccc2c3)cc1]
(70)
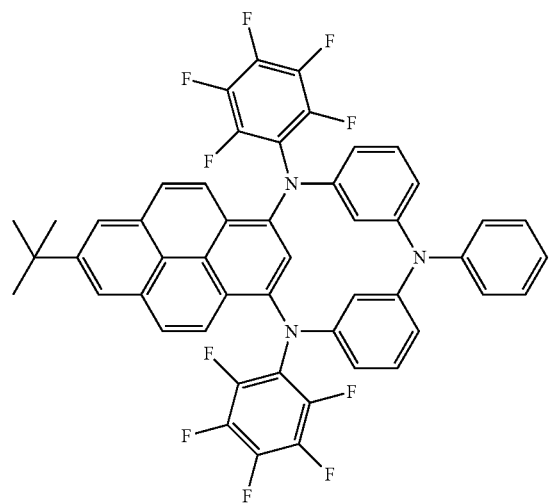 [SMILES: CC(C)(C)c1cc2ccc3c4cc(c5ccc(c1)c2c35)N(c1c(F)c(F)c(F)c(F)c1F)c1cccc(c1)N(c1ccccc1)c1cccc(c1)N4c1c(F)c(F)c(F)c(F)c1F]

(71)
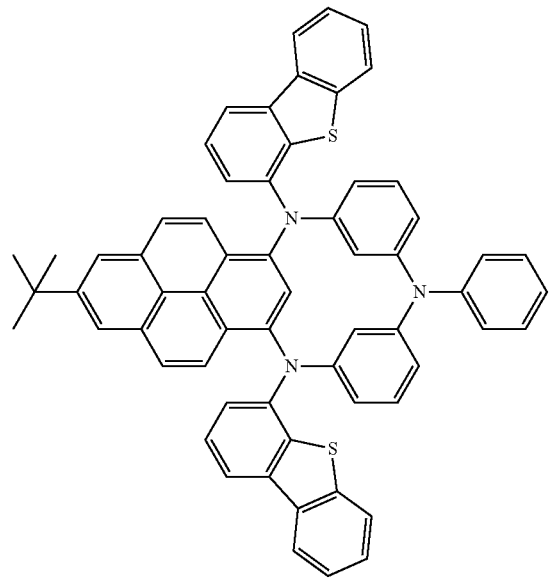 [SMILES: CC(C)(C)c1cc2ccc3c4cc(c5ccc(c1)c2c35)N(c1cccc2c1sc1ccccc12)c1cccc(c1)N(c1ccccc1)c1cccc(c1)N4c1cccc2c1sc1ccccc12]
(72)
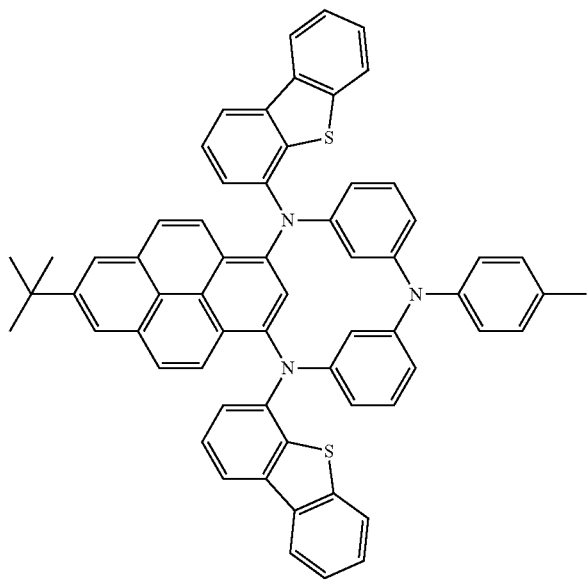 [SMILES: Cc1ccc(N2c3cccc(c3)N(c3cccc4c3sc3ccccc34)c3cc(c4ccc5cc(C(C)(C)C)cc6ccc3c4c65)N(c3cccc4c3sc3ccccc34)c3cccc2c3)cc1]

(73)
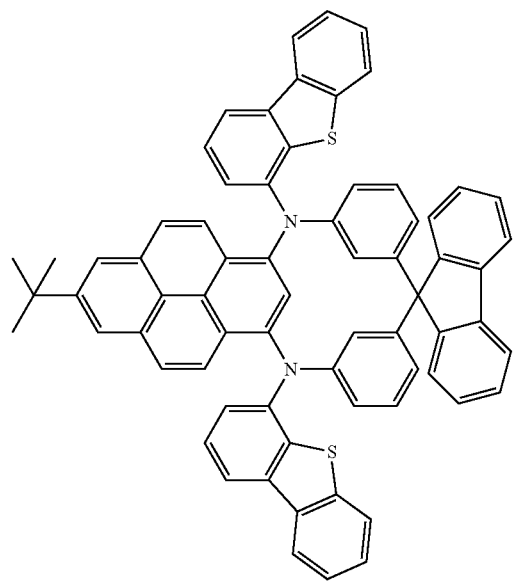 [SMILES: CC(C)(C)c1cc2ccc3c4cc(c5ccc(c1)c2c35)N(c1cccc2c1sc1ccccc12)c1cccc(c1)C1(c2cccc(c2)N4c2cccc3c2sc2ccccc23)c2ccccc2-c2ccccc21]
(74)
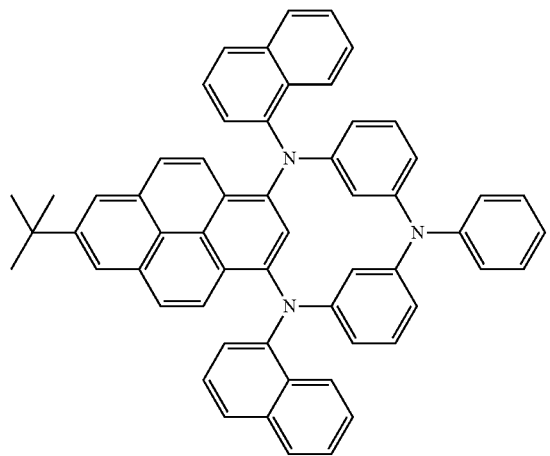 [SMILES: CC(C)(C)c1cc2ccc3c4cc(c5ccc(c1)c2c35)N(c1cccc2ccccc12)c1cccc(c1)N(c1ccccc1)c1cccc(c1)N4c1cccc2ccccc12]
(75)
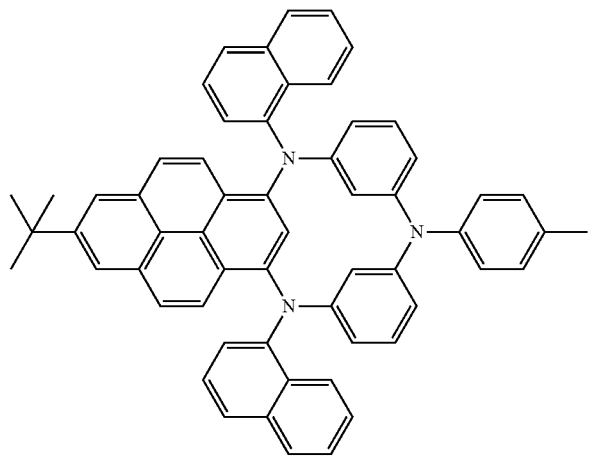 [SMILES: Cc1ccc(N2c3cccc(c3)N(c3cccc4ccccc34)c3cc(c4ccc5cc(C(C)(C)C)cc6ccc3c4c65)N(c3cccc4ccccc34)c3cccc2c3)cc1]

-continued
(76)
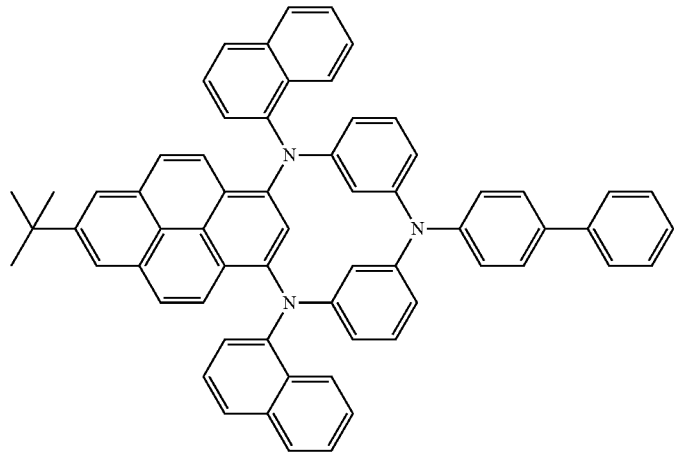 [SMILES: CC(C)(C)c1cc2ccc3c4cc(c5ccc(c1)c2c35)N(c1cccc2ccccc12)c1cccc(c1)N(c1ccc(-c2ccccc2)cc1)c1cccc(c1)N4c1cccc2ccccc12]
(77)
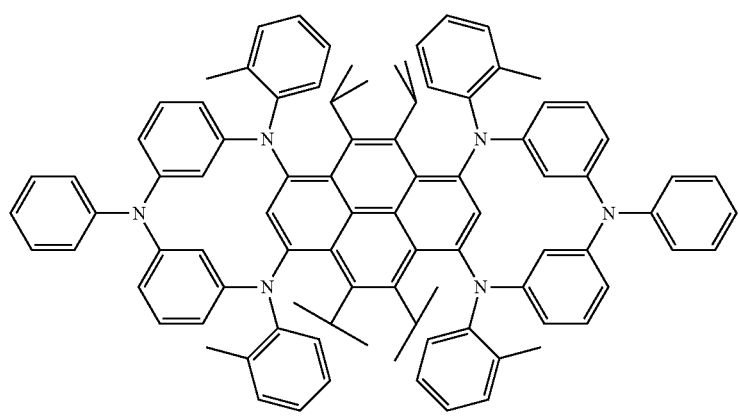 [SMILES: Cc1ccccc1N1c2cccc(c2)N(c2ccccc2)c2cccc(c2)N(c2ccccc2C)c2cc1c1c(C(C)C)c(C(C)C)c3c4cc(c5c(C(C)C)c(C(C)C)c2c1c35)N(c1ccccc1C)c1cccc(c1)N(c1ccccc1)c1cccc(c1)N4c1ccccc1C]
(78)
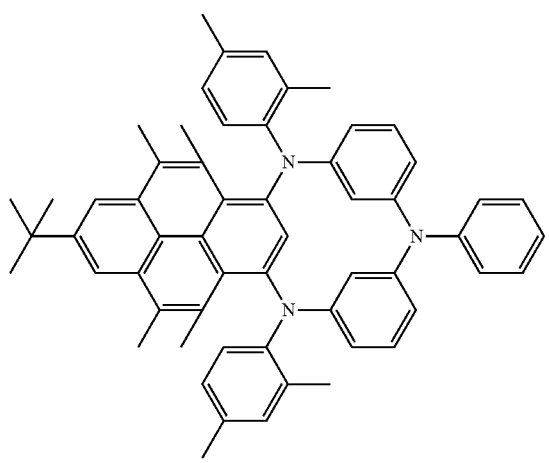 [SMILES: Cc1ccc(N2c3cccc(c3)N(c3ccccc3)c3cccc(c3)N(c3ccc(C)cc3C)c3cc2c2c(C)c(C)c4cc(C(C)(C)C)cc5c(C)c(C)c3c2c45)c(C)c1]

(79)
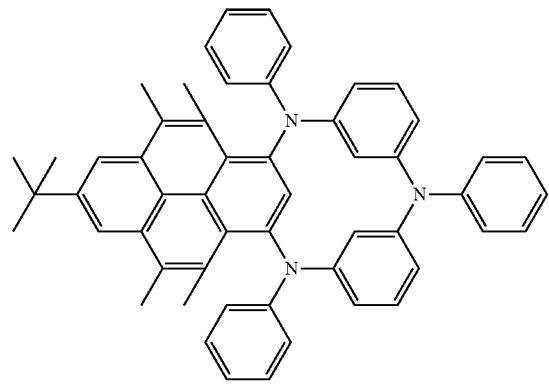 [SMILES: Cc1c(C)c2c3cc(c4c(C)c(C)c5cc(C(C)(C)C)cc1c5c24)N(c1ccccc1)c1cccc(c1)N(c1ccccc1)c1cccc(c1)N3c1ccccc1]
(80)
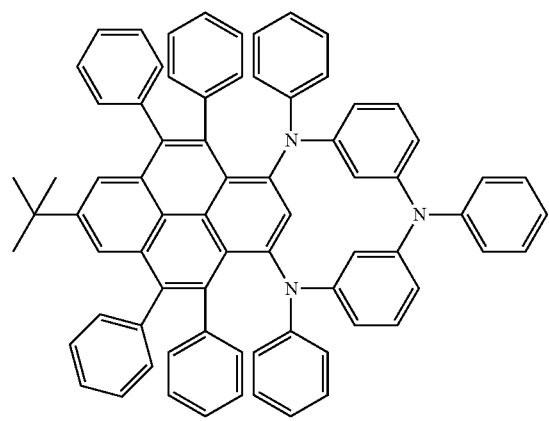 [SMILES: CC(C)(C)c1cc2c(-c3ccccc3)c(-c3ccccc3)c3c4cc(c5c(-c6ccccc6)c(-c6ccccc6)c(c1)c2c35)N(c1ccccc1)c1cccc(c1)N(c1ccccc1)c1cccc(c1)N4c1ccccc1]
(81)
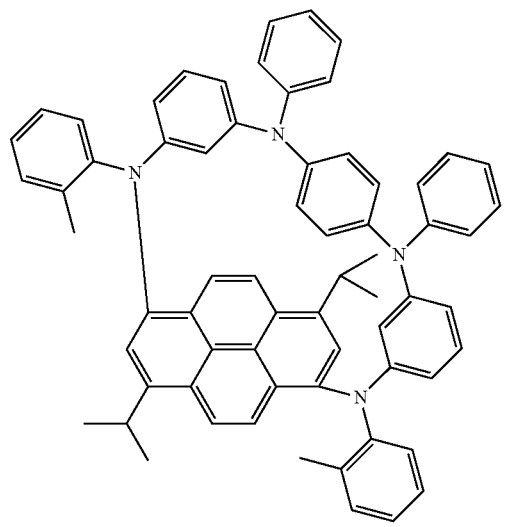 [SMILES: Cc1ccccc1N1c2cccc(c2)N(c2ccccc2)c2ccc(cc2)N(c2ccccc2)c2cccc(c2)N(c2ccccc2C)c2cc(C(C)C)c3ccc4c1cc(C(C)C)c1ccc2c3c14]

(82)
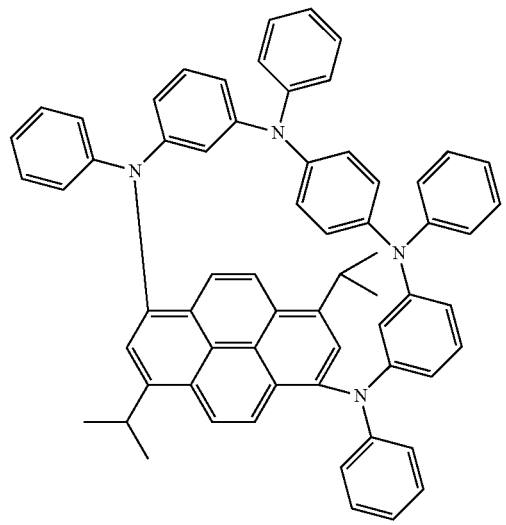 [SMILES: CC(C)c1cc2c3ccc4c(C(C)C)cc(c5ccc1c3c45)N(c1ccccc1)c1cccc(c1)N(c1ccccc1)c1ccc(cc1)N(c1ccccc1)c1cccc(c1)N2c1ccccc1]
(83)
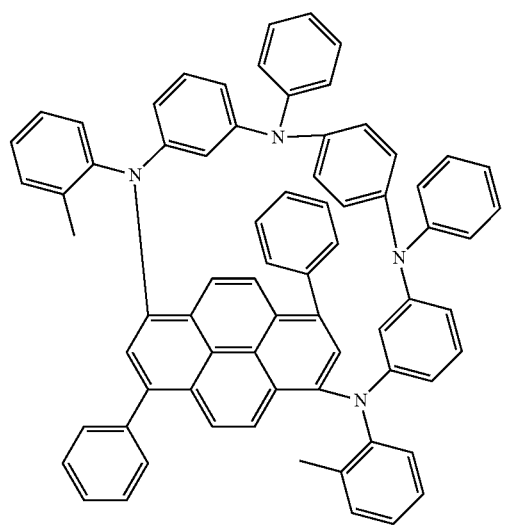 [SMILES: Cc1ccccc1N1c2cccc(c2)N(c2ccccc2)c2ccc(cc2)N(c2ccccc2)c2cccc(c2)N(c2ccccc2C)c2cc(-c3ccccc3)c3ccc4c1cc(-c1ccccc1)c1ccc2c3c14]
(84)
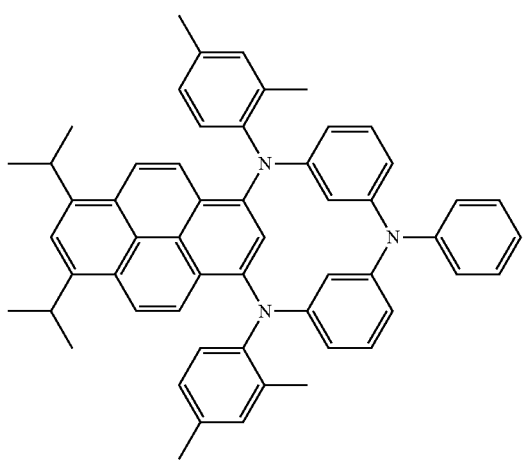 [SMILES: Cc1ccc(N2c3cccc(c3)N(c3ccccc3)c3cccc(c3)N(c3ccc(C)cc3C)c3cc2c2ccc4c(C(C)C)cc(C(C)C)c5ccc3c2c45)c(C)c1]

-continued
(85)
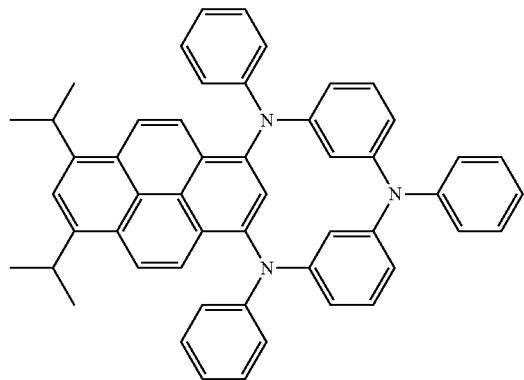 [SMILES: CC(C)c1cc(C(C)C)c2ccc3c4cc(c5ccc1c2c53)N(c1ccccc1)c1cccc(c1)N(c1ccccc1)c1cccc(c1)N4c1ccccc1]
(86)
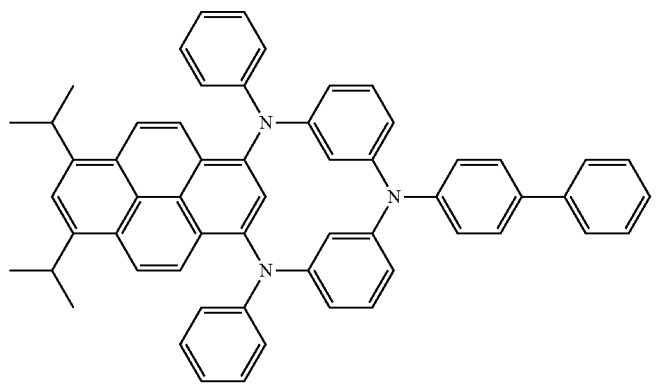 [SMILES: CC(C)c1cc(C(C)C)c2ccc3c4cc(c5ccc1c2c53)N(c1ccccc1)c1cccc(c1)N(c1ccc(-c2ccccc2)cc1)c1cccc(c1)N4c1ccccc1]
(87)
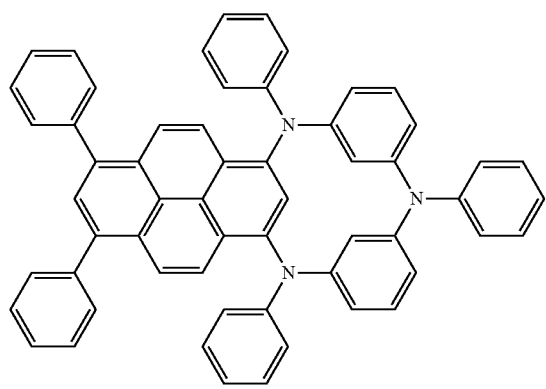 [SMILES: c1ccc(-c2cc(-c3ccccc3)c3ccc4c5cc(c6ccc2c3c64)N(c2ccccc2)c2cccc(c2)N(c2ccccc2)c2cccc(c2)N5c2ccccc2)cc1]
(88)
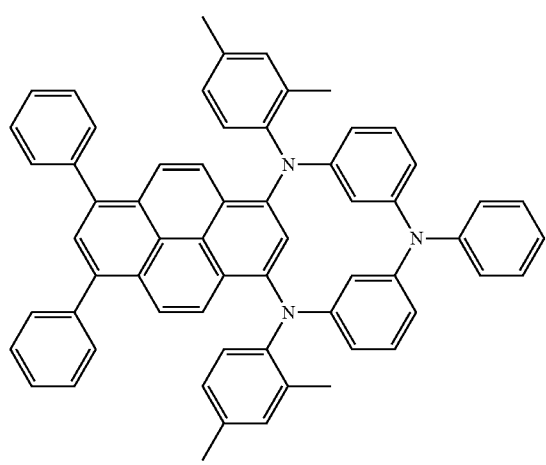 [SMILES: Cc1ccc(N2c3cccc(c3)N(c3ccccc3)c3cccc(c3)N(c3ccc(C)cc3C)c3cc2c2ccc4c(-c5ccccc5)cc(-c5ccccc5)c5ccc3c2c45)c(C)c1]

-continued
(89)
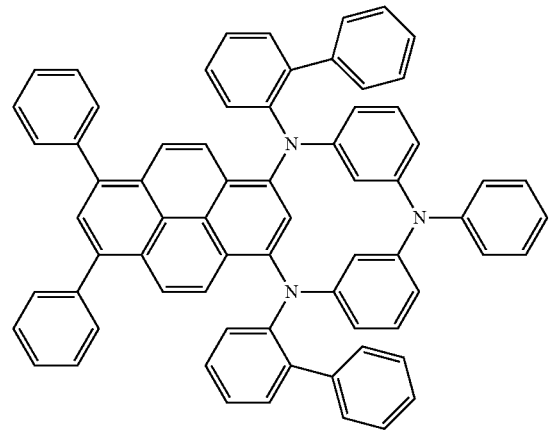 [SMILES: c1ccc(-c2ccccc2N2c3cccc(c3)N(c3ccccc3)c3cccc(c3)N(c3ccccc3-c3ccccc3)c3cc2c2ccc4c(-c5ccccc5)cc(-c5ccccc5)c5ccc3c2c45)cc1]
(90)
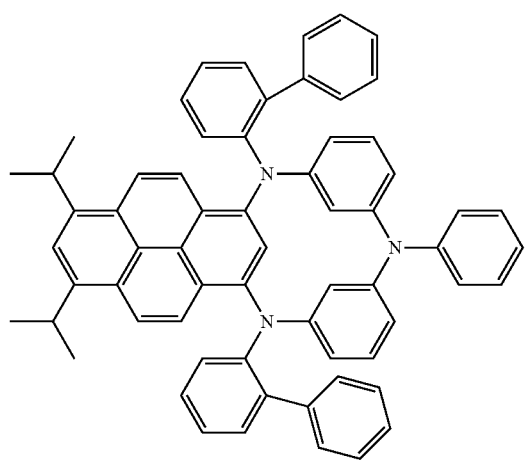 [SMILES: CC(C)c1cc(C(C)C)c2ccc3c4cc(c5ccc1c2c53)N(c1ccccc1-c1ccccc1)c1cccc(c1)N(c1ccccc1)c1cccc(c1)N4c1ccccc1-c1ccccc1]
(91)
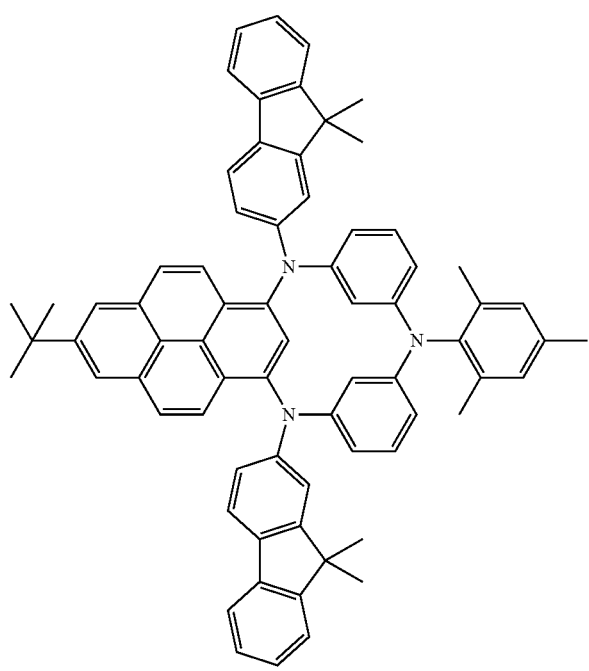 [SMILES: Cc1cc(C)c(N2c3cccc(c3)N(c3ccc4c(c3)C(C)(C)c3ccccc3-4)c3cc(c4ccc5cc(C(C)(C)C)cc6ccc3c4c65)N(c3ccc4c(c3)C(C)(C)c3ccccc3-4)c3cccc2c3)c(C)c1]

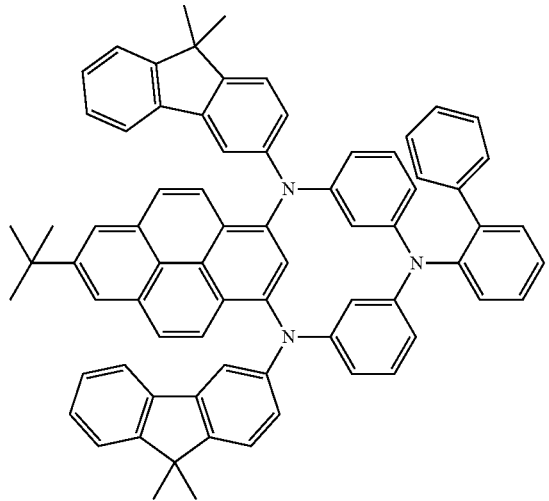 [SMILES: CC(C)(C)c1cc2ccc3c4cc(c5ccc(c1)c2c35)N(c1ccc2c(c1)-c1ccccc1C2(C)C)c1cccc(c1)N(c1ccccc1-c1ccccc1)c1cccc(c1)N4c1ccc2c(c1)-c1ccccc1C2(C)C]

(92)

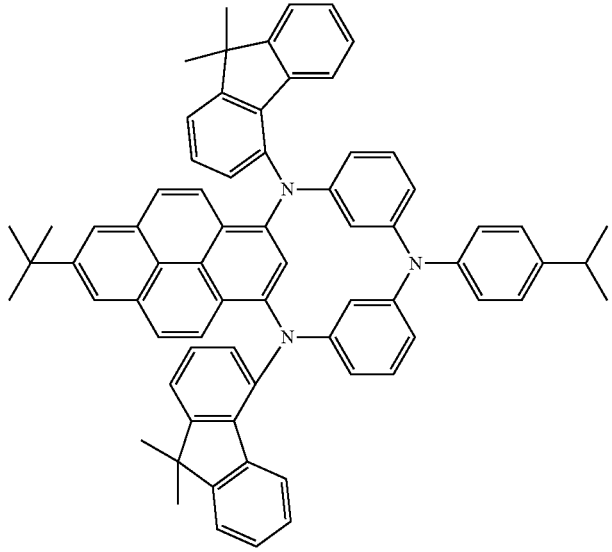 [SMILES: CC(C)c1ccc(N2c3cccc(c3)N(c3cccc4c3-c3ccccc3C4(C)C)c3cc(c4ccc5cc(C(C)(C)C)cc6ccc3c4c65)N(c3cccc4c3-c3ccccc3C4(C)C)c3cccc2c3)cc1]

(93)

The present application furthermore relates to a process for the preparation of a compound of the formula (I).

Preference is given to a process for the preparation of a compound of the formula (I), characterised in that it includes at least one transition metal-catalysed coupling reaction. The coupling reaction is preferably selected from Buchwald coupling reactions. One of the two reactants in the Buchwald coupling is preferably a pyrene derivative which carries two or more amino groups. The Buchwald coupling preferably introduces a link between two amino groups which are bonded to the pyrene derivative.

Preferred processes for the preparation of the compounds of the formula (I) are described below. Possible synthesis processes with which the person skilled in the art will be able to prepare the compounds are thereby proposed to him. However, the person skilled in the art is not tied to the processes presented. If necessary, he will be able to modify them within the bounds of his general expert knowledge if this is necessary.

According to one variant of the process, firstly two monoarylamino groups are introduced onto the pyrene skeleton, preferably via a Buchwald coupling. This gives a pyrene derivative containing two secondary arylamino groups. In a further step, preferably a Buchwald coupling, a group $Ar^1$—X—$Ar^1$ which connects the two arylamino groups to one another is then introduced. The group $Ar^1$—X—$Ar^1$ as reactive building block can be prepared in a few steps or is commercially available. Specific examples of syntheses of this group are included in the working examples. The said step may optionally be followed by further functionalisation steps in which the compound is modified further. The compound may be substituted as desired.

Scheme 1

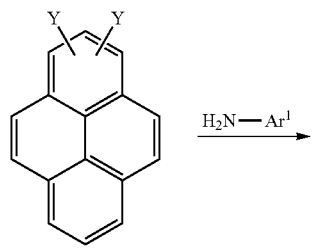

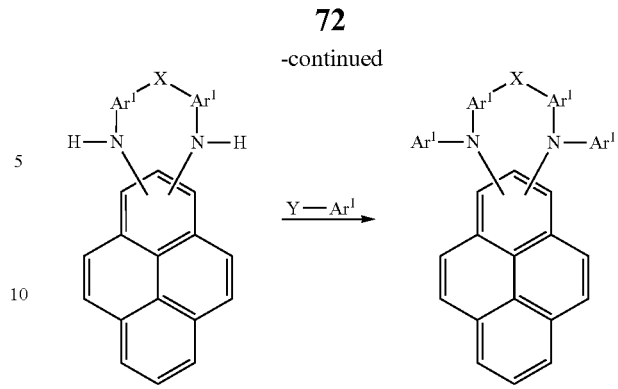

X = bridging group, preferably CR$_2$, SiR$_2$, NR, O, S
Y = reactive group, preferably Cl, Br, I
Ar$^1$ = aromatic or heteroaromatic ring system
R = any desired organic radical

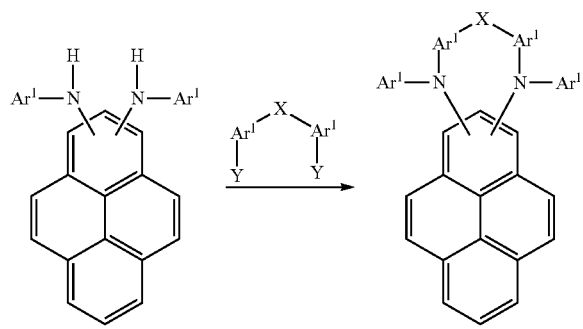

X = bridging group, preferably CR$_2$, SiR$_2$, NR, O, S
Y = reactive group, preferably Cl, Br, I
Ar$^1$ = aromatic or heteroaromatic ring system
R = any desired organic radical According to another variant, firstly two NH$_2$ groups are introduced onto the pyrene skeleton. This gives a pyrene derivative containing two primary amino groups. In a further step, preferably a Buchwald coupling, a group Ar$^1$—X—Ar$^1$, as presented above, which connects the two arylamino groups to one another is then introduced. This gives a pyrene derivative containing two secondary arylamino groups, where the aryl groups are linked to one another. In a second step, the secondary arylamino groups are then converted into tertiary arylamino groups, preferably by a second Buchwald coupling to a further aryl group. The said step may optionally be followed by further functionalisation steps in which the compound is modified further. The compound may be substituted as desired.

Scheme 2

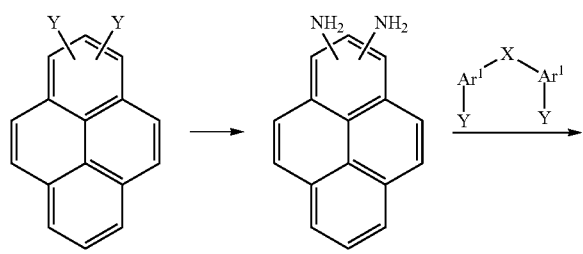

The compounds of the formula (I) described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (I), where the bond(s) to the polymer, oligomer or dendrimer may be localised at any desired positions in formula (I) which are substituted by R$^1$, R$^2$ or R$^3$. Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, a-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) according to the invention are suitable for use in electronic devices, in particular in organic electroluminescent devices (OLEDs). Depending on the substitution, the compounds are employed in various functions and layers.

The invention therefore furthermore relates to the use of a compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (I). The electronic device is preferably selected from the devices indicated above. Particular preference is given to an organic electroluminescent device comprising anode, cathode and at least one emitting layer, characterised in that at least one organic layer comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the organic electroluminescent device is preferably as follows: anode/hole-injection layer/hole-transport layer/emitting layer/electron-transport layer/electron-injection layer/cathode. However, it is not necessary for all of the said layers to be present, and/or additional layers may be present.

The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

It is preferred for the compound of the formula (I) to be present in an emitting layer. The compound of the formula (I) is particularly suitable for use as emitting compound in an emitting layer.

The compound according to the invention is particularly suitable for use as blue-emitting compound. The relevant electronic device here may comprise a single emitting layer comprising the compound according to the invention, or it may comprise two or more emitting layers. The further emitting layers here may comprise one or more compounds according to the invention or alternatively other compounds.

If the compound according to the invention is employed as emitting compound in an emitting layer, it is preferably employed in combination with one or more matrix materials. The matrix material is preferably present here in a higher proportion than the emitting compound. For the purposes of the present application, matrix material of the emitting layer is taken to mean a material which has no emitting function.

It is also possible for a plurality of emitting compounds to be present simultaneously in the emitting layer. However, this is preferably not the case.

According to an embodiment of the invention, two or more matrix compounds, preferably precisely two, are present in the emitting layer (mixed-matrix system). One of the two matrix materials here is preferably a material having hole-transporting properties and the other matrix material is a material having electron-transporting properties.

However, the desired electron-transporting and hole-transporting properties of the mixed-matrix components may also be combined principally or entirely in a single mixed-matrix component, where the further mixed-matrix components fulfil other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems can be employed in phosphorescent emitting layers and in fluorescent emitting layers. More precise details on mixed-matrix systems can be found, inter alia, in WO 2010/108579 and in the as yet unpublished applications EP 13000014.4 and EP 13000015.1.

The proportion of the compound according to the invention in the mixture of the emitting layer is preferably between 0.1 and 50.0% by vol., particularly preferably between 0.5 and 20.0% by vol., and very particularly preferably between 1.0 and 10.0% by vol. Correspondingly, the proportion of the matrix material or matrix materials is preferably between 50.0 and 99.9% by vol., particularly preferably between 80.0 and 99.5% by vol., and very particularly preferably between 90.0 and 99.0% by vol.

Preferred matrix materials for use in combination with the materials according to the invention are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for use in combination with the compound of the formula (I) in the emitting layer are depicted in the following table.

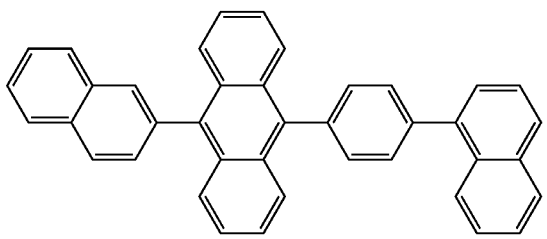 [SMILES: c1ccc2cc(-c3c4ccccc4c(-c4ccc(-c5cccc6ccccc56)cc4)c4ccccc34)ccc2c1]

-continued
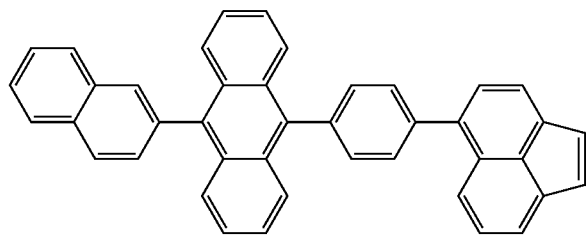 [SMILES: C1=Cc2ccc(-c3ccc(-c4c5ccccc5c(-c5ccc6ccccc6c5)c5ccccc45)cc3)c3cccc1c23]
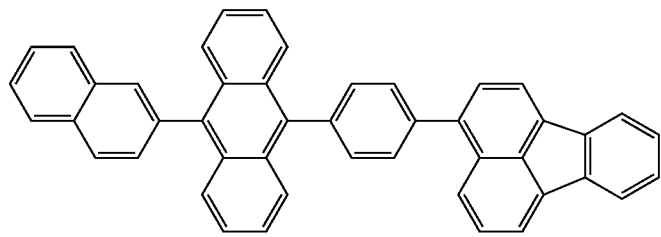 [SMILES: c1ccc2c(c1)-c1cccc3c(-c4ccc(-c5c6ccccc6c(-c6ccc7ccccc7c6)c6ccccc56)cc4)ccc-2c13]
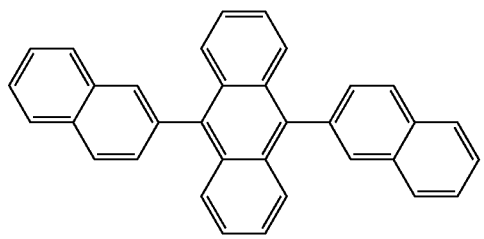 [SMILES: c1ccc2cc(-c3c4ccccc4c(-c4ccc5ccccc5c4)c4ccccc34)ccc2c1]
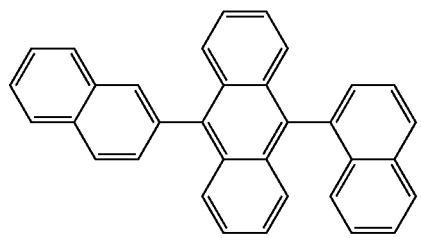 [SMILES: c1ccc2cc(-c3c4ccccc4c(-c4cccc5ccccc45)c4ccccc34)ccc2c1]
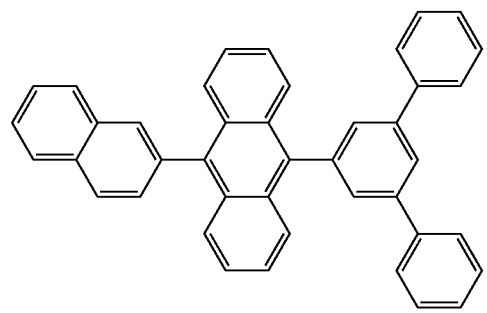 [SMILES: c1ccc(-c2cc(-c3ccccc3)cc(-c3c4ccccc4c(-c4ccc5ccccc5c4)c4ccccc34)c2)cc1]
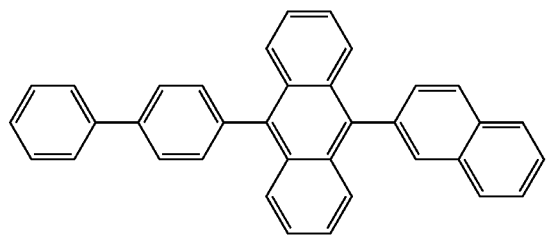 [SMILES: c1ccc(-c2ccc(-c3c4ccccc4c(-c4ccc5ccccc5c4)c4ccccc34)cc2)cc1]

-continued
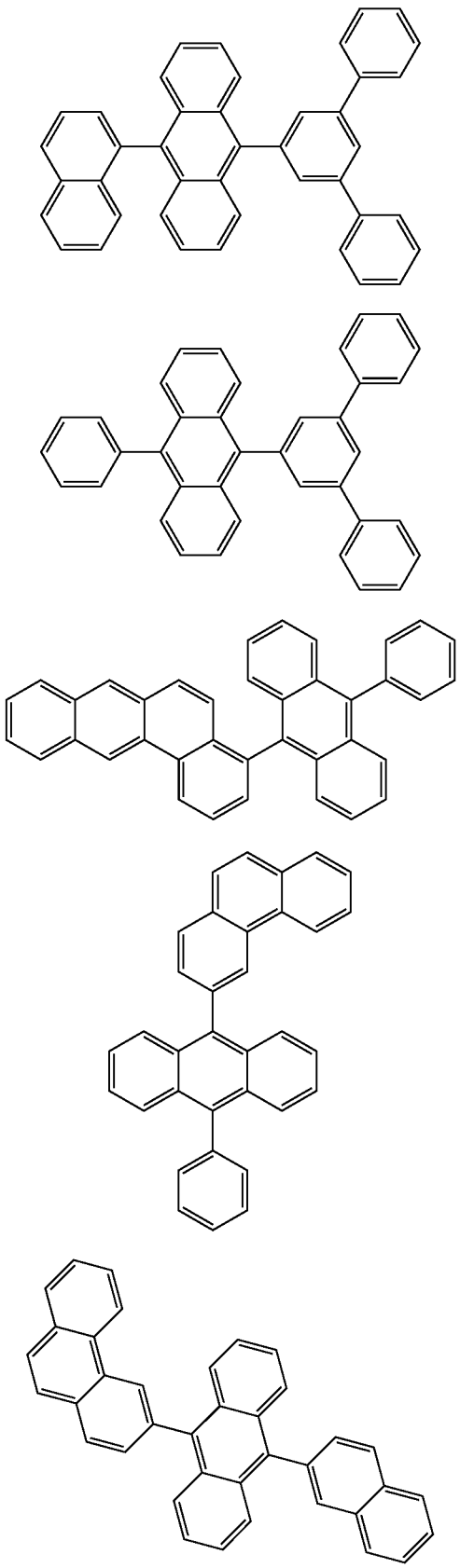

-continued
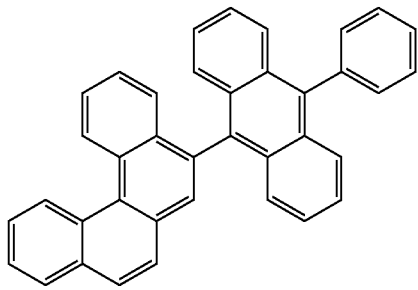 [SMILES: c1ccc(-c2c3ccccc3c(-c3cc4ccc5ccccc5c4c4ccccc34)c3ccccc23)cc1]

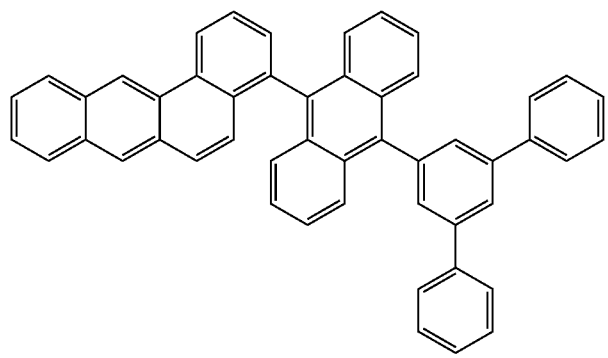 [SMILES: c1ccc(-c2cc(-c3ccccc3)cc(-c3c4ccccc4c(-c4cccc5c4ccc4cc6ccccc6cc45)c4ccccc34)c2)cc1]
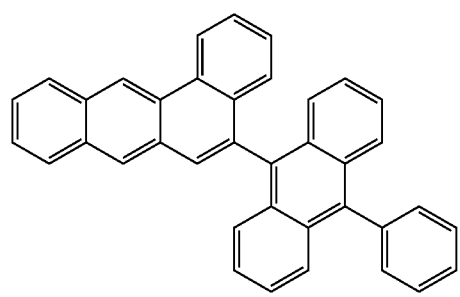 [SMILES: c1ccc(-c2c3ccccc3c(-c3cc4cc5ccccc5cc4c4ccccc34)c3ccccc23)cc1]
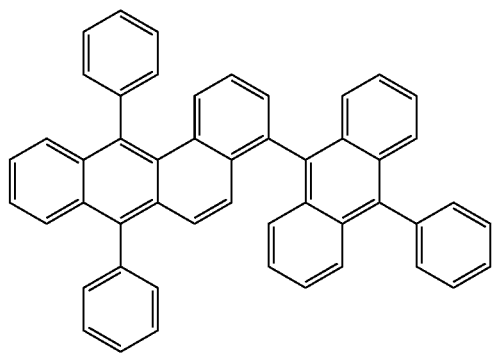 [SMILES: c1ccc(-c2c3ccccc3c(-c3cccc4c3ccc3c(-c5ccccc5)c5ccccc5c(-c5ccccc5)c34)c3ccccc23)cc1]
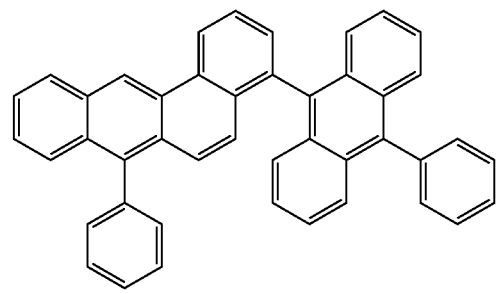 [SMILES: c1ccc(-c2c3ccccc3c(-c3cccc4c3ccc3c(-c5ccccc5)c5ccccc5cc34)c3ccccc23)cc1]
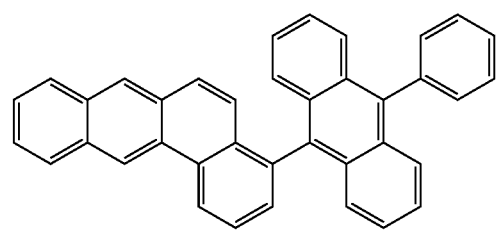 [SMILES: c1ccc(-c2c3ccccc3c(-c3cccc4c3ccc3cc5ccccc5cc34)c3ccccc23)cc1]

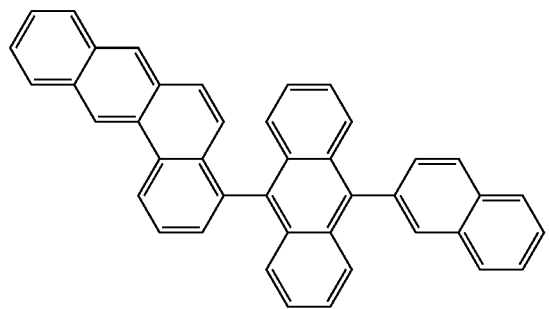 [SMILES: c1ccc2cc(-c3c4ccccc4c(-c4cccc5c4ccc4cc6ccccc6cc45)c4ccccc34)ccc2c1]
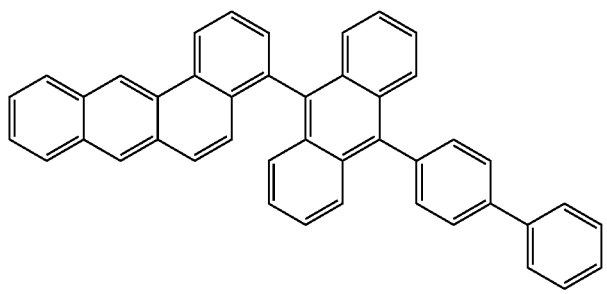 [SMILES: c1ccc(-c2ccc(-c3c4ccccc4c(-c4cccc5c4ccc4cc6ccccc6cc45)c4ccccc34)cc2)cc1]
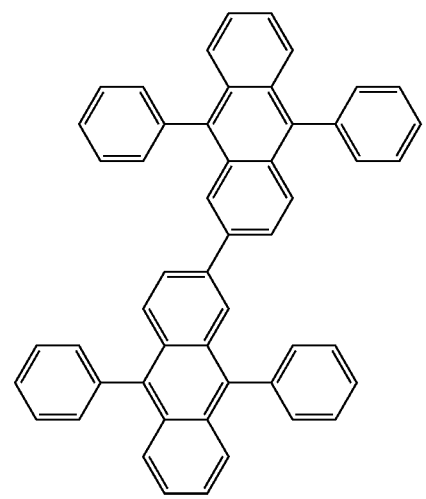 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
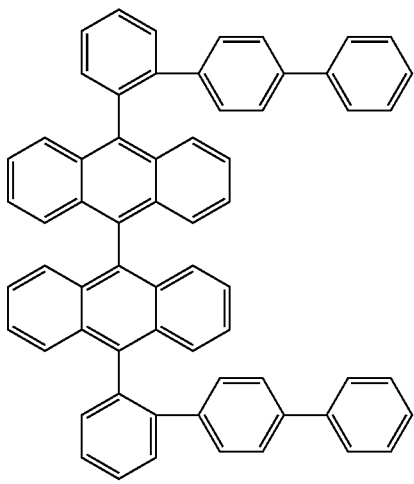 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]

-continued
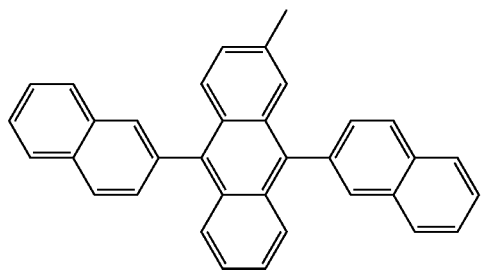 [SMILES: Cc1ccc2c(-c3ccc4ccccc4c3)c3ccccc3c(-c3ccc4ccccc4c3)c2c1]
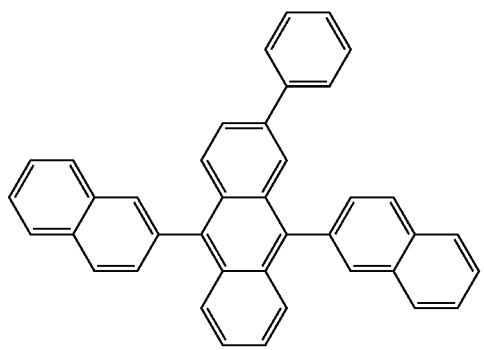 [SMILES: c1ccc(-c2ccc3c(-c4ccc5ccccc5c4)c4ccccc4c(-c4ccc5ccccc5c4)c3c2)cc1]
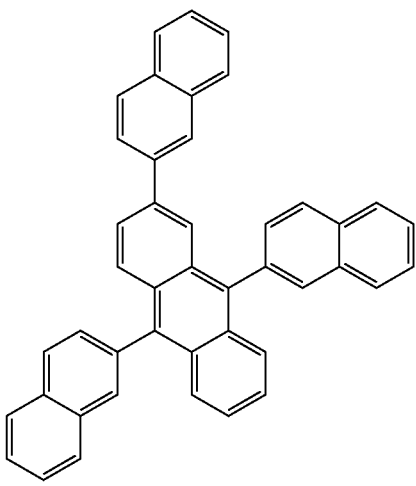 [SMILES: c1ccc2cc(-c3ccc4c(-c5ccc6ccccc6c5)c5ccccc5c(-c5ccc6ccccc6c5)c4c3)ccc2c1]
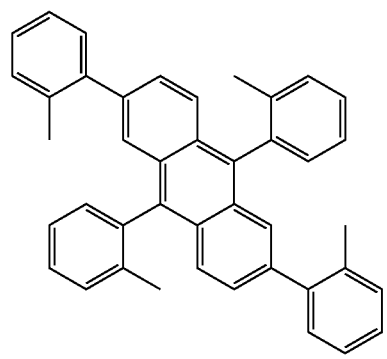 [SMILES: Cc1ccccc1-c1ccc2c(-c3ccccc3C)c3cc(-c4ccccc4C)ccc3c(-c3ccccc3C)c2c1]

-continued
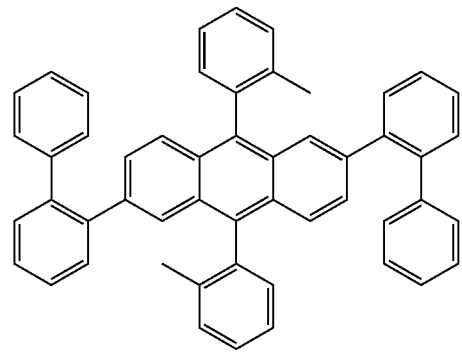 [SMILES: Cc1ccccc1-c1c2ccc(-c3ccccc3-c3ccccc3)cc2c(-c2ccccc2C)c2ccc(-c3ccccc3-c3ccccc3)cc12]
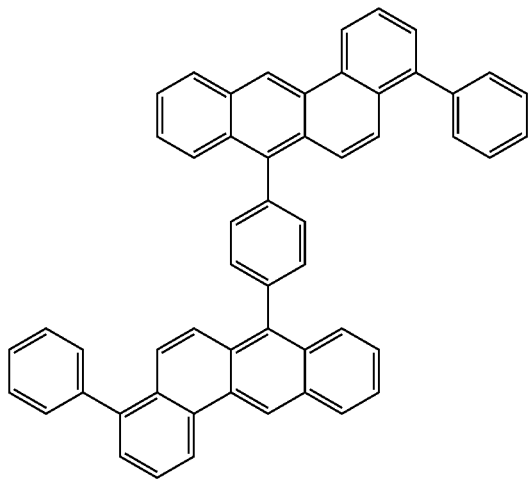 [SMILES: c1ccc(-c2cccc3c2ccc2c(-c4ccc(-c5c6ccccc6cc6c5ccc5c(-c7ccccc7)cccc56)cc4)c4ccccc4cc23)cc1]
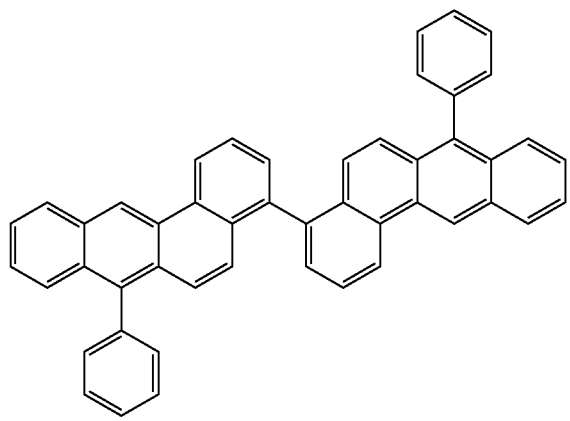 [SMILES: c1ccc(-c2c3ccccc3cc3c2ccc2c(-c4cccc5c4ccc4c(-c6ccccc6)c6ccccc6cc45)cccc23)cc1]
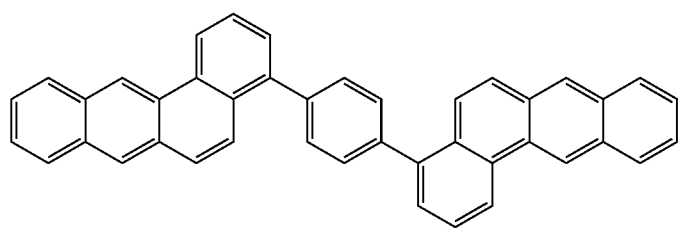 [SMILES: c1ccc2cc3c(ccc4c(-c5ccc(-c6cccc7c6ccc6cc8ccccc8cc67)cc5)cccc43)cc2c1]

-continued
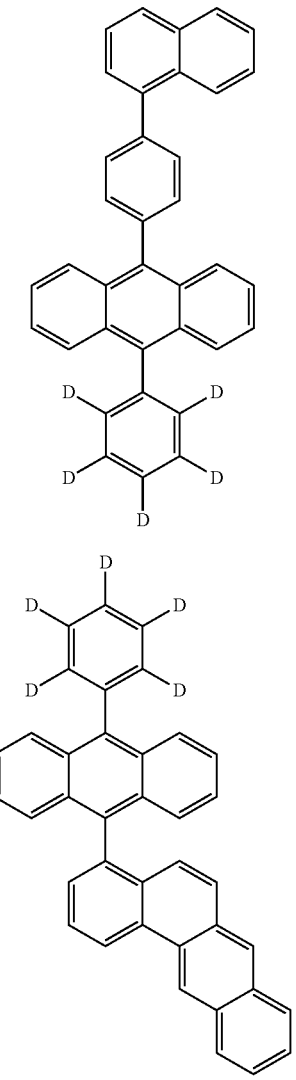
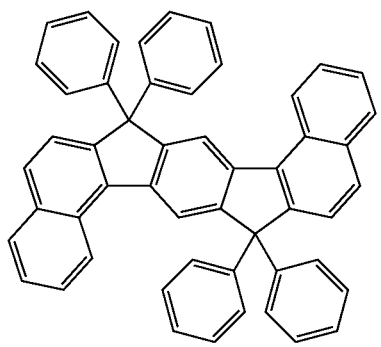 [SMILES: c1ccc(C2(c3ccccc3)c3cc4c(cc3-c3c2ccc2ccccc32)C(c2ccccc2)(c2ccccc2)c2ccc3ccccc3c2-4)cc1]
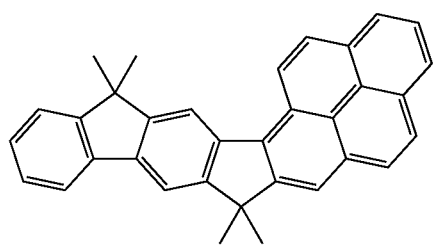 [SMILES: CC1(C)c2ccccc2-c2cc3c(cc21)-c1c(cc2ccc4cccc5ccc1c2c45)C3(C)C]

-continued
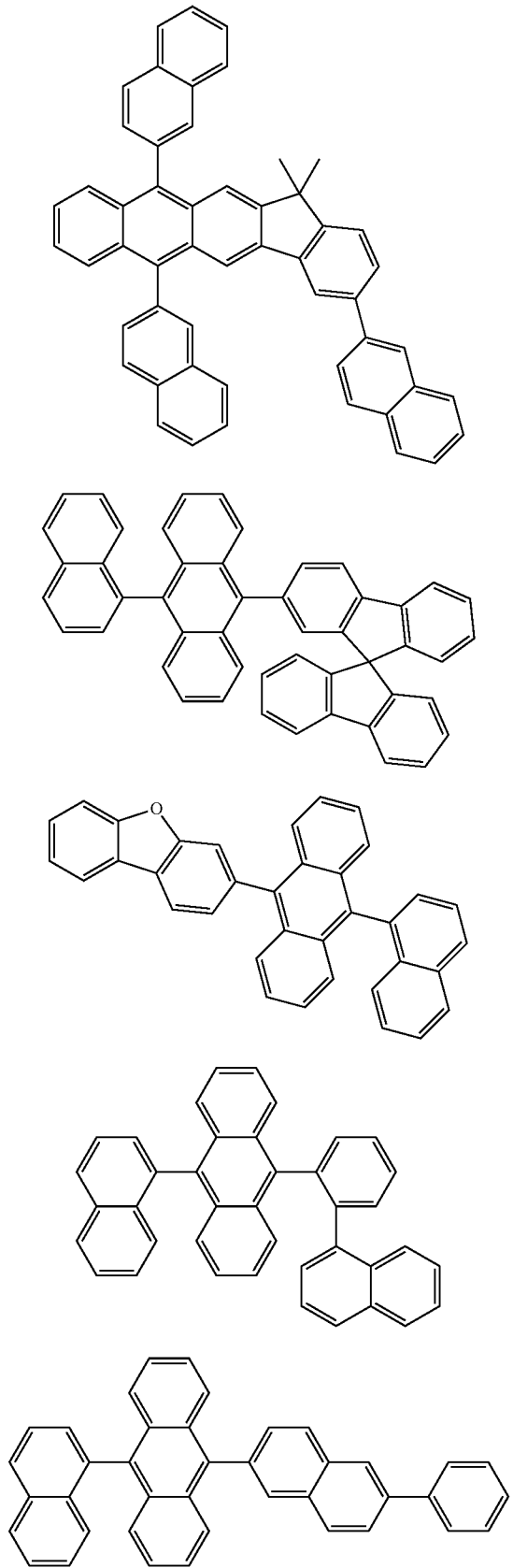

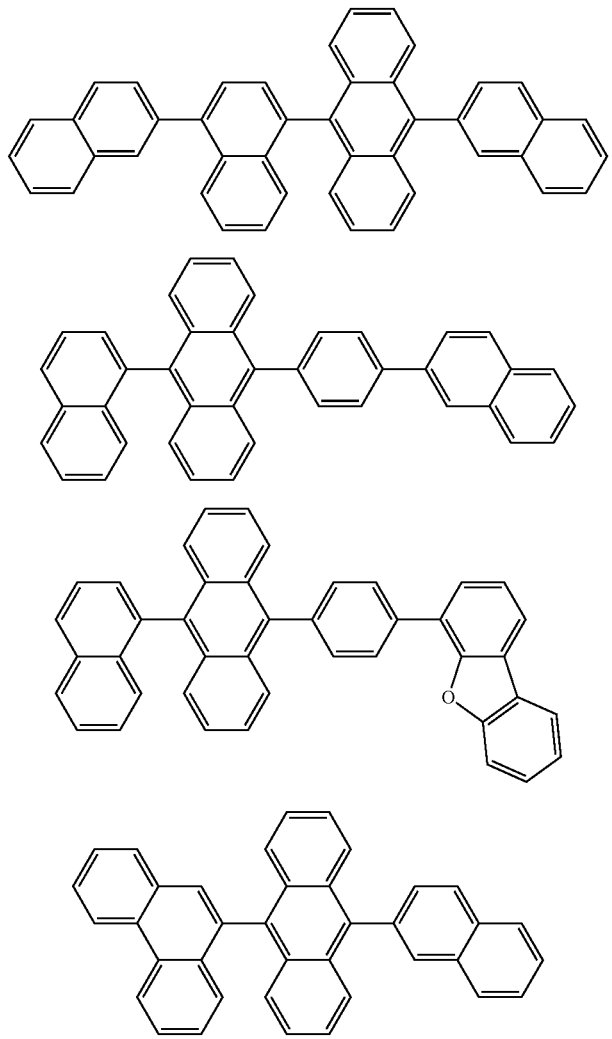

The compounds according to the invention can also be employed in other layers, for example in a hole-transport layer or a hole-injection layer.

Generally preferred classes of material for use as corresponding functional materials in the organic electroluminescent devices according to the invention are indicated below.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of the phosphorescent emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Preferred fluorescent emitters, besides the compounds according to the invention, are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Preferred matrix materials for use with fluorescent emitters are indicated above.

Preferred matrix materials for phosphorescent emitters are aromatic amines, in particular triarylamines, for example in accordance with US 2005/0069729, carbazole derivatives (for example CBP, N,N-bis-carbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, and diazaphosphole derivatives, for example in accordance with WO 2010/054730.

Suitable charge-transport materials, as can be used in the hole-injection or hole-transport layer or electron-blocking layer or in the electron-transport layer of the organic electroluminescent device according to the invention, besides the compounds according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used in a hole-transport, hole-injection or electron-blocking layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives with condensed aromatic rings (for example in accordance with U.S. Pat. No. 5,061,569), the amine derivatives disclosed in WO 95/09147, monobenzoindenofluorenamines (for example in accordance with WO 08/006449) or dibenzoindenofluorenamines (for example in accordance with WO 07/140847). Furthermore suitable hole-transport- and hole-injection materials are derivatives of the compounds depicted above, as are disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

Aniline, 1,3-dibromobenzene, 1,2-dibromobenzene, phenol, N,N-dimethylcarbamoyl chloride, 1-bromo-3-iodobenzene, 2-bromobiphenyl, 1-bromobenzene, 2-bromo-1,3-dimethylbenzene, 1-bromo-2-fluorobenzene, o-tolylamine, 4-bromodibenzofuran, 2,4-dimethylphenylamine and 2-fluorophenylamine are commercially available. The synthesis of 1,3-dibromo-7-tert-butylpyrene is described in *Adv. Mat*, 2010, 22, 990-993.

Variant I:

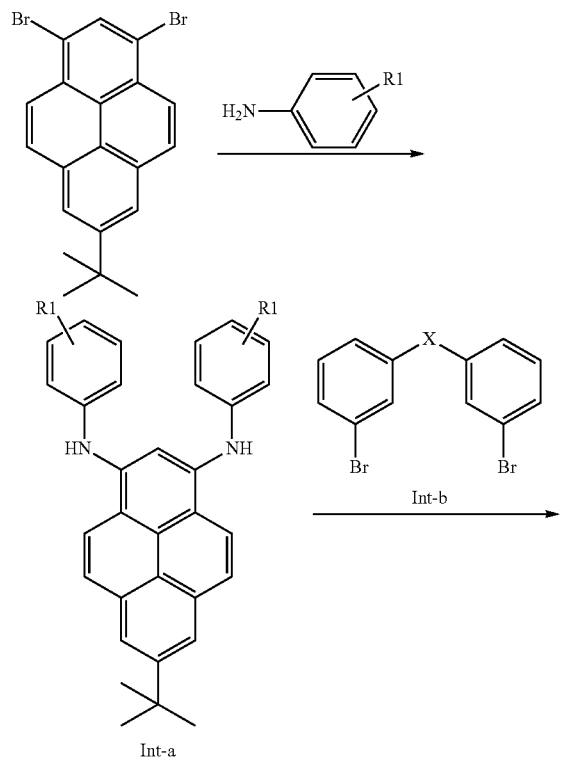

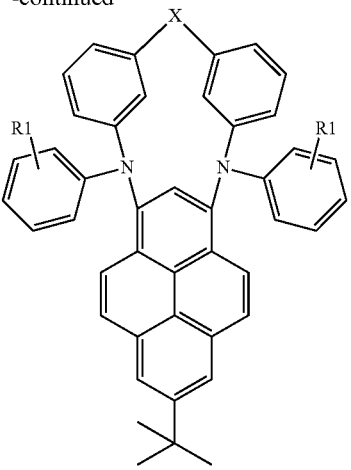

Compound Int-a-1

1,3-Dibromo-7-tert-butylpyrene (20.0 g, 48.1 mmol) and aniline (15.7 g, 168.2 mmol) are dissolved in 300 ml of toluene. Sodium tert-butoxide (13.9 g, 144 mmol) is then added. The solution is degassed and saturated with argon. 1,1'-Bis(diphenylphosphino)ferrocene (2.1 g, 3.85 mmol) and palladium(II) acetate (431 mg, 1.92 mmol) are subsequently added. The reaction mixture is heated under reflux under protective-gas atmosphere for 4 h. The mixture is filtered through silica gel and AlOx. After filtration of the crude product, the residue which remains is recrystallised from a heptane/toluene mixture, giving 21.2 g (79% of theory) of the product as yellow solid.

The following compounds are prepared analogously:

| Compound | Pyrene | Arylamine | Product |
|---|---|---|---|
| Int-a-2 | | | |

| Int-a-3 | 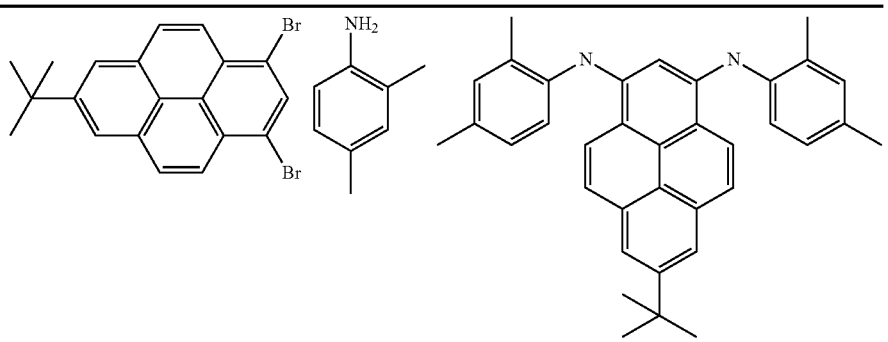 | | |
|---|---|---|---|
| Int-a-4 | 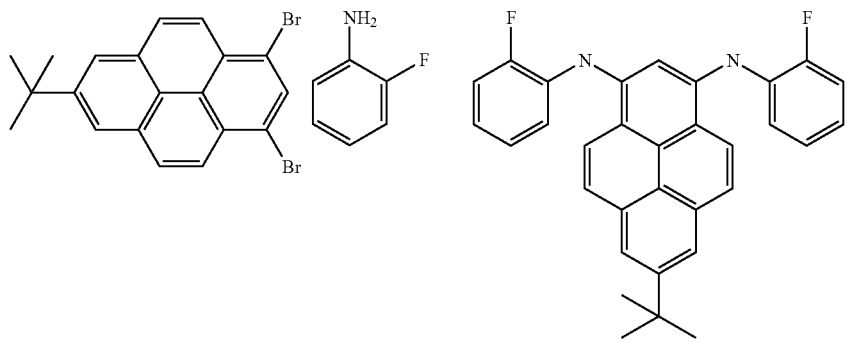 | | |
| Compound | Yield |
|---|---|
| Int-a-2 | 91% |
| Int-a-3 | 32% |
| Int-a-4 | 41% |
Synthesis of the Bridging Groups Int-b-1 to Int-b-3
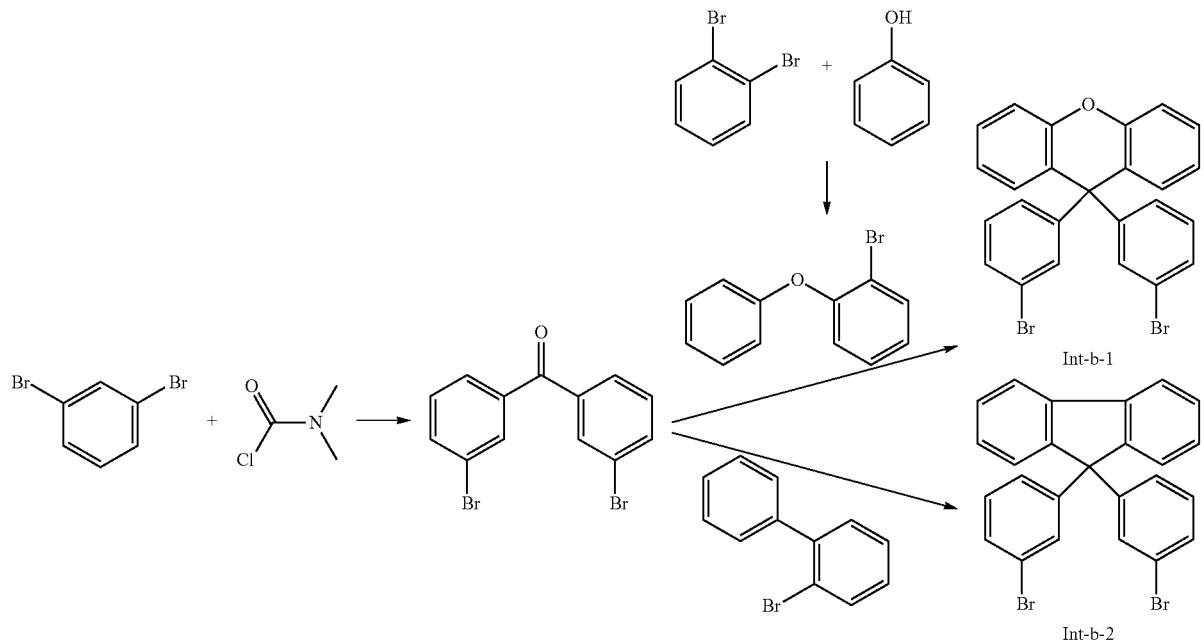

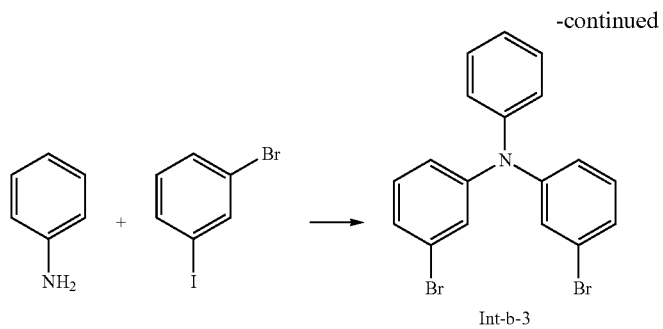

Int-b-3

Bis-(3-bromophenyl)methanone 1,3-Dibromobenzene (59.0 g, 250 mmol) is dissolved in 1.1 l of diethyl ether and cooled to −65° C. 100 ml of n-BuLi solution (2.5 M in n-hexane) is slowly added dropwise, and the mixture is stirred for a further 1 h. N,N-Dimethylcarbamoyl chloride is added in one portion with vigorous stirring.

The mixture is stirred at −65° C. for 1 h and then warmed slowly. A mixture of 250 ml of water and 25 ml of acetic acid is subsequently slowly added dropwise. The product precipitates out as white solid. The solid is filtered off with suction and rinsed with water and ethanol. The yield is 42.2 g (76% of theory) as white solid.

1-Bromo-2-phenoxybenzene 1,2-Dibromobenzene (451.1 g, 1.9 mol), phenol (150.0 g, 1.50 mol), potassium carbonate (132.2 g, 956 mmol) and copper(I) oxide (273.7 g, 1.9 mol) are mixed, and glass beads are added. The reaction mixture is stirred at an internal temperature of 180° C. overnight. The batch is cooled, and then diluted with 300 ml of DCM. The batch solution is filtered through a Büchner funnel, and then through Celite. The filtrate is evaporated in a rotary evaporator. The oil is distilled under a high vacuum (1.5 mbar, head temperature 135° C.). 168.1 g of white solid are isolated (45% of theory).

9,9-Bis-(3-bromophenyl)-9H-xanthene (Int-b-1)

Magnesium (3.17 g, 120.6 mmol) is initially introduced in a flask with one crystal of iodine. 1-Bromo-2-phenoxybenzene (23.2 g, 93.2 mmol), 190 ml of anhydrous THF, 26 ml of 1,2-dimethoxyethane and 0.78 ml of 1,2-dichloroethane are initially introduced in a dropping funnel. The starting-material mixture is slowly added dropwise. The reaction is stirred at 70° C. for a further 3 h and then cooled. Bis(3-bromophenyl)methanone (32 g, 93.2 mmol) is dissolved in 200 ml of THF and slowly added dropwise. The reaction is stirred under reflux for 4 h. The batch is subsequently filtered, and the THF is removed in a rotary evaporator. 400 ml of acetic acid and 75 ml of concentrated hydrochloric acid are added, and the mixture is stirred at 75° C. for 4 h, before 200 ml of water are added. The pale solid is filtered off with suction and washed with methanol. The solid is stirred in boiling ethyl acetate for 1 h, filtered and washed with ethanol. The yield is 28.2 g (62% of theory) as white solid.

9,9-Bis-(3-bromophenyl)-9H-fluorene (Int-b-2)

Magnesium (6.73 g, 255.8 mmol) is initially introduced in a flask with one crystal of iodine. 2-Bromobiphenyl (64.4 g, 276.3 mmol), 400 ml of anhydrous THF, 500 ml of anhydrous toluene, 45 ml of 1,2-dimethoxyethane and 2.65 ml of 1,2-dichloroethane are introduced into a dropping funnel. The starting-material mixture is slowly added dropwise. The reaction is stirred under reflux for a further 1 h, and subsequently cooled. Bis-(3-bromophenyl)methanone (61.4 g, 180.6 mmol) is dissolved in 600 ml of THF and slowly added dropwise. The reaction is stirred under reflux for 5 h. The batch is filtered, and the THF is evaporated in a rotary evaporator. 500 ml of glacial acetic acid, 200 ml of acetic acid and 10 ml of HBr are added, and the mixture is stirred under reflux for 64 h. The pale solid is filtered off with suction and washed with ethyl acetate and ethanol. The yield is 79.8 g (92% of theory) as white solid.

Bis-(3-bromophenyl)phenylamine (Int-b-3)

1-Bromo-3-iodobenzene (200.5 g, 708.7 mmol), aniline (30.0 g, 322 mmol), copper(I) iodide (4.92 g, 25.8 mmol), potassium hydroxide (145.8 g, 2.58 mol) and 1,10-phenanthroline (4.67 g, 25.8 mmol) are suspended in 1 l of o-xylene. The solution is degassed and saturated with argon. The reaction mixture is stirred under reflux overnight. The mixture is filtered through silica gel and AlOx with toluene and subsequently evaporated in a rotary evaporator. The pale-brown solid is filtered off with suction. The solid is then purified by column chromatography (heptane). The product is stirred under reflux in heptane for 3 h and then filtered. The yield is 58.6 g (45% of theory) as white solid.

7-tert-Butyl-N,N'-diphenylpyrene-1,3-diamine, Bridged to 9,9-bis-(3-bromophenyl)-9H-xanthene (1)

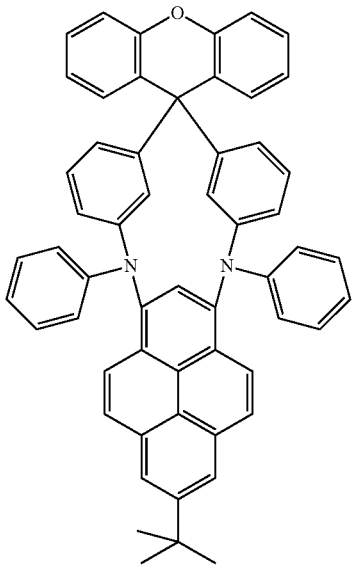 [SMILES: CC(C)(C)c1cc2ccc3c4cc(c5ccc(c1)c2c35)N(c1ccccc1)c1cccc(c1)C1(c2cccc(c2)N4c2ccccc2)c2ccccc2Oc2ccccc21]

Sodium tert-butoxide (16.6 g, 173 mmol) is suspended in 500 ml of toluene. The solution is degassed and saturated with argon. 7-tert-Butyl-N,N'-diphenylpyrene-1,3-diamine (19.0 g, 43.1 mmol) and 9,9-bis(3-bromophenyl)-9H-xanthene (21.2 g, 43.1 mmol) are dissolved in 1.8 l of THF, saturated with argon and introduced into a dropping funnel. Tri-tert-butylphosphine (1 M solution in toluene, 15.5 ml, 15.5 mmol) and palladium(II) acetate (2.32 g, 10.4 mmol) are then added to the base/toluene solution, and the mixture is heated under reflux. The starting-material mixture is subsequently added dropwise. The reaction is stirred for a further 2 h. The batch is filtered twice through silica gel and AlOx and evaporated in a rotary evaporator. The solid is extracted with toluene in a Soxhlet extractor and recrystallised from toluene. The yield is 1.9 g (6% of theory) as yellow solid.

The following compounds are prepared analogously:

| Example compound | Starting material | Product | Yield |
|---|---|---|---|
| 2 | Int-a-2 | | 7% |
| 3 | Int-a-3 | | 3% |

-continued
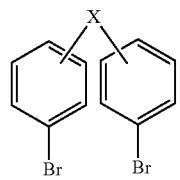
| Example compound | Starting material | | Product | Yield |
|---|---|---|---|---|
| 4 | Int-a-1 | 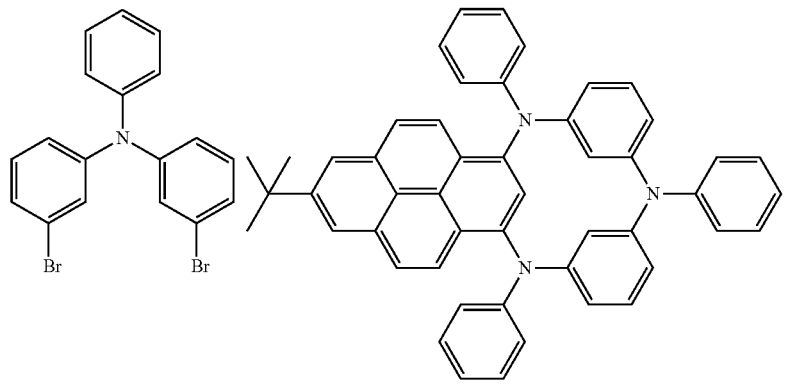 | | 29% |
| 5 | Int-a-4 | 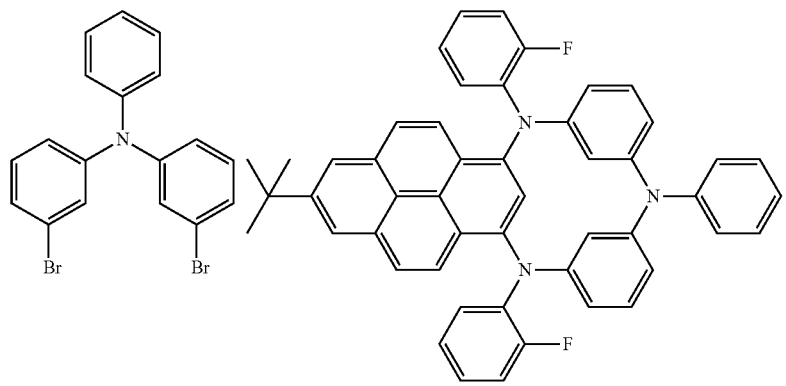 | | 3% |
| 6 | Int-a-1 | 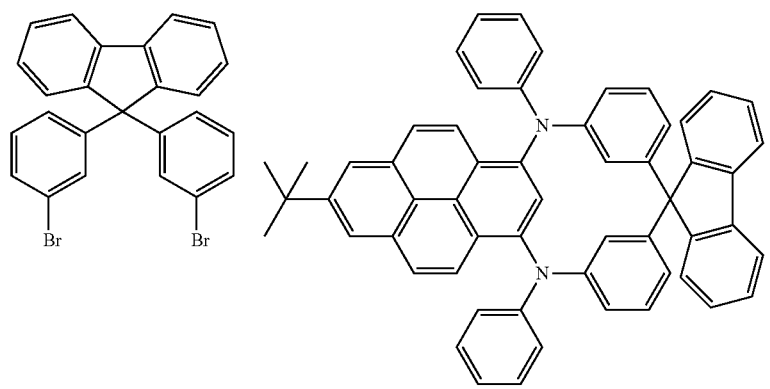 | | 24% |

Variant II:

Synthesis of N,N'-bisbiphenyl-2-yl-7-tert-butylpyrene-1,3-diamine Bridged to triphenylamine (7)

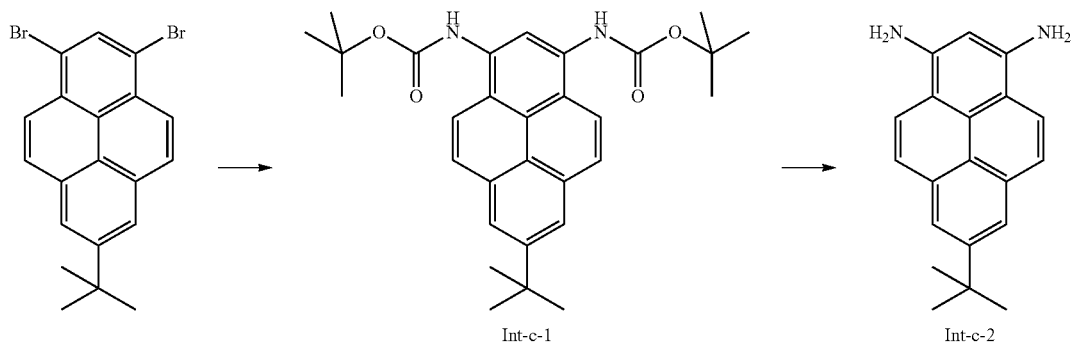

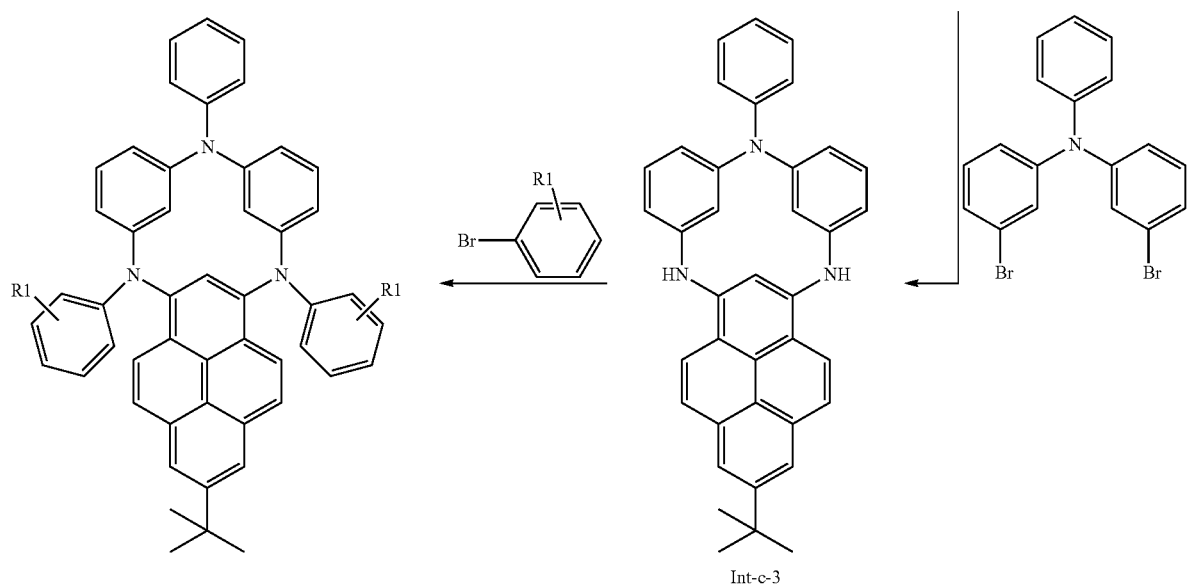

tert-Butyl (3-tert-butoxycarbonylamino-7-tert-butylpyren-1-yl)carbamate (Int-c-1)

1,3-Dibromo-7-tert-butylpyrene (5 g, 12 mmol), tert-butyl carbamate (3.66 g, 31.2 mmol) and caesium carbonate (12.5 g, 38.5 mmol) are suspended in 100 ml of anhydrous dioxane. The solution is degassed and saturated with argon. 9,9-Dimethyl-4,5-bis(diphenylphosphino)xanthene (556 mg, 0.96 mmol) and palladium(II) acetate (162 mg, 0.72 mmol) are added. The reaction is stirred under reflux overnight. The reaction mixture is filtered and extracted with heptane and then toluene in a Soxhlet extractor. The product is obtained as brown solid: 2.6 g (46% of theory).

7-tert-Butylpyrene-1,3-diamine (Int-c-2)

tert-Butyl (3-tert-butoxycarbonylamino-7-tert-butylpyren-1-yl)carbamate (5.9 g, 12 mmol) is dissolved in 50 ml of DCM. Trifluoroacetic acid (11 g, 97 mmol) is added. The batch is stirred under reflux for 2 h and subsequently evaporated. The solid is dissolved in toluene and filtered through AlOx. The product is eluted over a silica-gel column with heptane/ethyl acetate 1:1. The yield is 615 mg (17.7% of theory) as black solid.

7-tert-Butylpyrene-1,3-diamine, Bridged to triphenylamine (Int-c-3)

Sodium tert-butoxide (615 mg, 6 mmol) is suspended in 60 ml of dioxane. The solution is degassed and saturated with argon. 7-tert-Butylpyrene-1,3-diamine (615 mg, 2.13 mmol) and bis(3-bromophenyl)phenylamine (860 mg, 2.13 mmol) are dissolved in 100 ml of dioxane, saturated with argon and initially introduced in a dropping funnel. S-Phos (52.6 mg, 0.128 mmol) and palladium(II) acetate (52.3 mg, 0.064 mmol) are then added to the base/dioxane solution, and the reaction mixture is heated to reflux. The starting-material mixture is added dropwise. The reaction is stirred for a further 2 h. The batch is filtered twice through silica gel and AlOx and evaporated in a rotary evaporator. The yield is 883 mg (78.2% of theory) as black oil.

111

N,N'-Bisbiphenyl-2-yl-7-tert-butylpyrene-1,3-diamine, Bridged to triphenylamine (7)

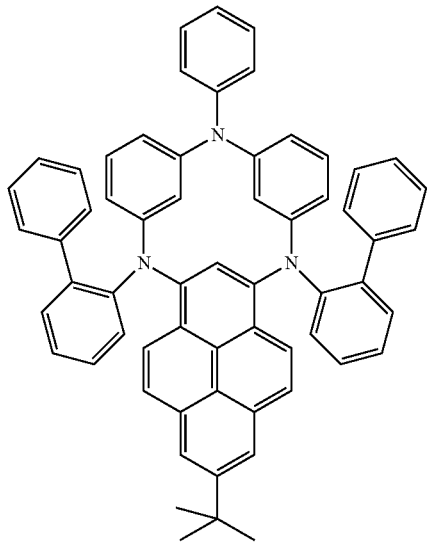 [SMILES: CC(C)(C)c1cc2ccc3c4cc(c5ccc(c1)c2c35)N(c1ccccc1-c1ccccc1)c1cccc(c1)N(c1ccccc1)c1cccc(c1)N4c1ccccc1-c1ccccc1]

112

The starting material Int-c-3 (318 mg, 0.600 mmol), 2-bromobiphenyl (490 mg, 2.1 mmol) and sodium tert-butoxide (173 mg, 1.8 mmol) are suspended in 30 ml of toluene. The solution is degassed and saturated with argon. Tri-tert-butylphosphine (1 M solution in toluene, 0.048 ml, 0.048 mmol) and palladium(II) acetate (11.6 mg, 0.024 mmol) are then added to the reaction mixture, which is then heated under reflux. The batch is filtered through silica gel and AlOx. The solid is eluted over a silica-gel column with heptane/ethyl acetate 5:1. The yield is 60 mg (12% of theory) as yellow solid.

The following compounds are prepared analogously:

| Example compound | Starting material 1 | Starting material 2 |
|---|---|---|
| 8 | | |
| 9 | | |
| 10 | | |

| Example compound | Product | Yield |
|---|---|---|
| 8 | 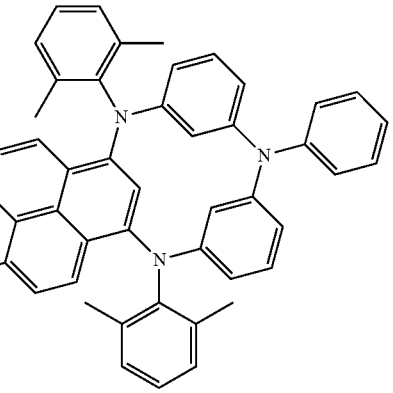 | 16% |
| 9 | 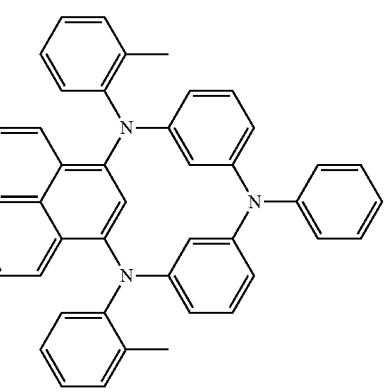 | 21% |
| 10 | 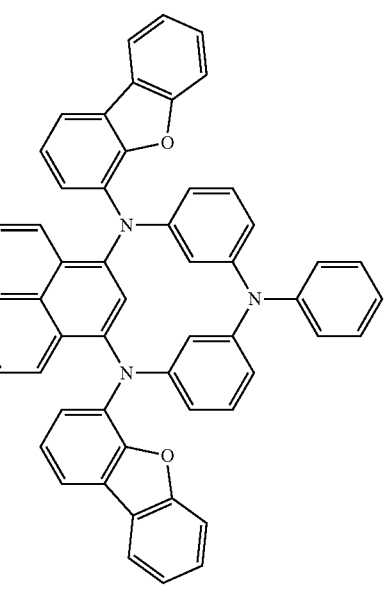 | 4% |

B) Measurement of the Temperature Stability

The behaviour of compound 4 according to the invention at high temperatures is investigated. In order to establish how high the temperature stability is, TGA measurements under protective gas of compound 4 and furthermore, for comparison, of the compound from the prior art SEBV1 are carried out (for the structures of the compounds cf. synthesis examples and Table 1 below).

Both samples are measured using a TGA Q 5000 instrument from TA Instruments. Both samples are heated in nitrogen atmosphere between room temperature and 600° C. at a heating rate of 20° C. per minute.

For compound 4, the temperature $T_x$ at which the mass has decreased by 5% is measured as 451° C.

For the comparative compound SEBV1, a temperature $T_x$ of 401° C. is measured under the same conditions.

The temperature stability is thus significantly better for compound 4 according to the invention than for the reference compound SEBV1.

C) Photoluminescence Measurements

Photoluminescence spectra of compound 3 according to the invention and of the compound SEBV2 known from the prior art are recorded in toluene at room temperature (concentration $10^{-5}$ g/mol). For the structures of the compounds cf. Table 1 below.

For compound 3 according to the invention, a CIE y coordinate of 0.077 is measured, a maximum of the emission at 447 nm, and a width of the emission band at half intensity compared with the maximum value (FWHM) of 44 nm.

For the comparative compound SEBV2, a CIE y coordinate of 0.090 is measured, a maximum of the emission at 450 nm, and a width of the emission band at half intensity compared with the maximum value (FWHM) of 45 nm.

A significantly deeper-blue colour impression (CIE y) with slightly shorter-wave emission and slightly smaller width of the emission band is thus measured for compound 3 according to the invention, compared with the compound in accordance with the prior art SEBV2.

D) Device Examples

The data of various OLEDs are presented in the following examples. OLEDs according to the invention and OLEDs in accordance with the prior art are produced by a general process in accordance with WO 04/058911, which is adapted to the circumstances described here (layer-thickness variation, materials).

The OLEDs have the following structure:

Glass plates coated with structured ITO (indium tin oxide) in a thickness of 50 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The general layer structure is the following: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm.

The precise structure of the OLEDs is revealed by the examples. The materials required for the production of the OLEDs are shown in Table 1.

All materials are applied by thermal vapour deposition in a vacuum chamber. The emission layer here always consists of at least one matrix material and an emitting compound which is admixed with the matrix material or matrix materials in a certain proportion by volume by co-evaporation. An expression such as H1(95%):SEBV1(5%) here means that material SEBV1 is present in the layer in a proportion by volume of 5% and H1 is present in the layer in a proportion of 95%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectrum are determined at a luminous density of 1000 cd/m², and the CIE 1931 x and y colour coordinates are calculated therefrom. The lifetime LT80 @ 60 mA is defined as the time after which the luminous density has dropped to 80% on operation with constant current of 60 mA/cm². The values for the lifetime can be converted into a figure for other initial luminous densities with the aid of conversion formulae known to the person skilled in the art.

The examples are explained in greater detail below in order to illustrate the properties and advantages of the OLEDs according to the invention. Even the improvement of a single parameter can represent a significant advance here, since different applications make different requirements with respect to individual parameters.

Materials 1 and 4 according to the invention are tested as emitters in blue-emitting OLEDs. Furthermore, an OLED comprising the emitter SEBV1 known from the prior art is produced.

The test structure used is the following structure: ITO/PEDOT (20 nm)/HTM1 (140 nm)/HIL1 (5 nm)/HTM2 (20 nm)/H1:x % of emitter (20 nm)/ETM1:50% of LiQ (30 nm)/Al.

Compound 1 according to the invention exhibits a colour coordinate CIE x/y of 0.137/0.100, (0.135/0.105), an EQE of 5.8% (6.4%) and a lifetime LT80 of 25 h (20 h) in the above test component in the case of 3%(5%) doping at 1000 cd/m².

Compound 4 according to the invention has a colour coordinate CIE x/y of 0.133/0.118, (0.134/0.117), an EQE of 6.6% (6.8%) and a lifetime LT80 of 47 h (31 h) under the same conditions in the case of 3%(5%) doping.

The reference emitter SEBV1 exhibits a colour coordinate CIE x/y of 0.137/0.102 (0.136/0.109), an EQE of 5.7% (5.8%) and a lifetime LT80 of 27 h (31 h) in the case of 3%(5%) doping at 1000 cd/m².

The materials according to the invention thus give rise to improvements over the prior art in all parameters, especially with respect to lifetime and efficiency, on use as emitters in OLEDs.

TABLE 1
Structural formulae of the materials used for the OLEDs
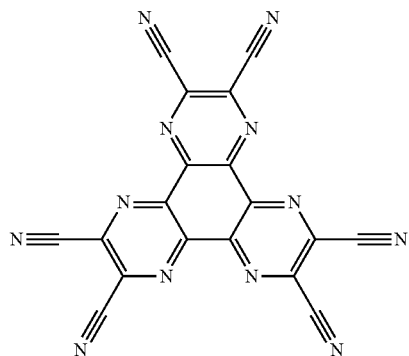 [SMILES: N#Cc1nc2c3nc(C#N)c(C#N)nc3c3nc(C#N)c(C#N)nc3c2nc1C#N] HIL1
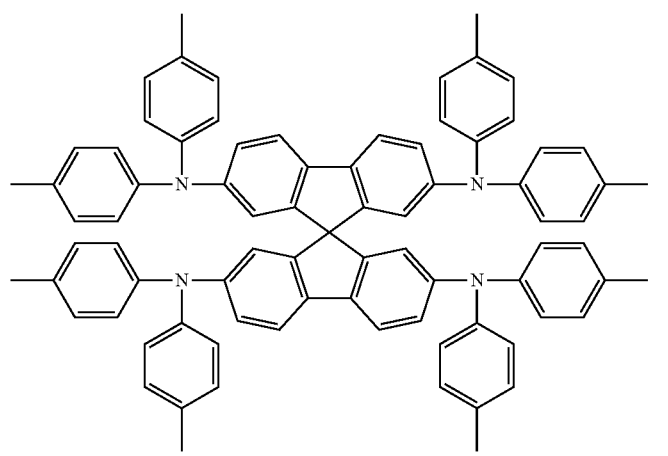 HTM1
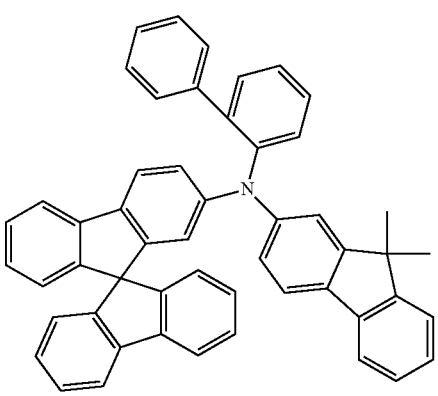 [SMILES: CC1(C)c2ccccc2-c2ccc(N(c3ccc4c(c3)C3(c5ccccc5-c5ccccc53)c3ccccc3-4)c3ccccc3-c3ccccc3)cc21] HTM2
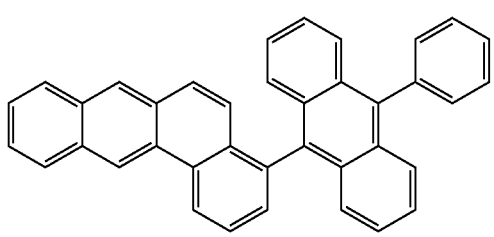 [SMILES: c1ccc(-c2c3ccccc3c(-c3cccc4c3ccc3cc5ccccc5cc34)c3ccccc23)cc1] H1

TABLE 1-continued
Structural formulae of the materials used for the OLEDs
SEBV1
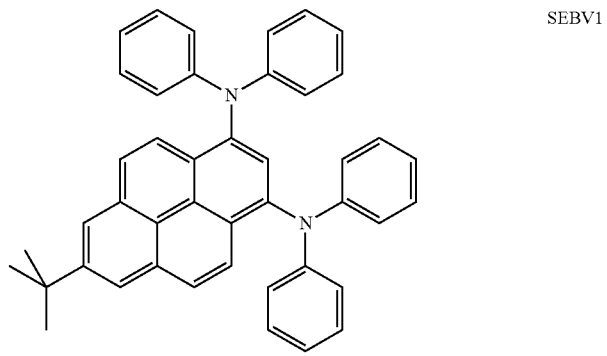
SEBV2
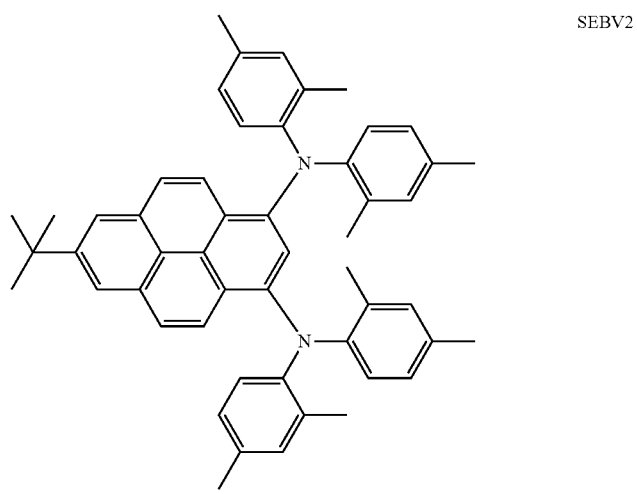
ETM1
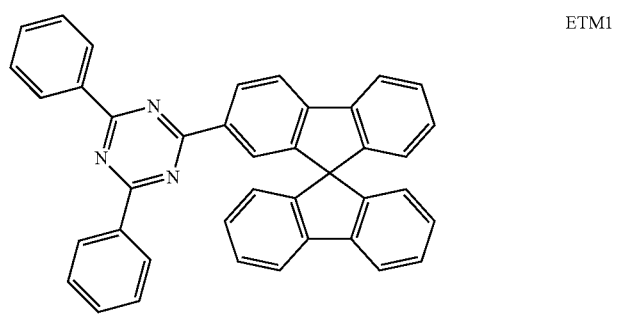
LiQ

The invention claimed is:
1. A compound of formulae (I-1), (I-2), or (I-3):

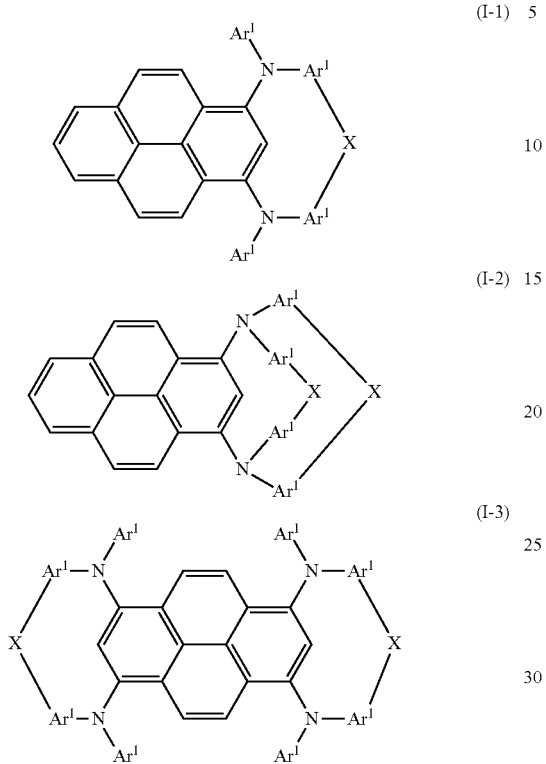

the pyrene groups of which are optionally substituted by a radical $R^1$ at each free position;

$Ar^1$ is on each occurrence, identically or differently, an aromatic or heteroaromatic ring system having 6 to 30 aromatic ring atoms, which is optionally substituted by one or more radicals $R^3$, and wherein groups $Ar^1$ are optionally linked via groups X;

X is on each occurrence, identically or differently, a single bond, or a divalent group selected from an aryl or heteroaryl group having 6 to 20 aromatic ring atoms, which is optionally substituted by one or more radicals $R^2$, or $BR^2$, $C(R^2)_2$, $-R^2C=CR^2-$, $C(=O)$, $Si(R^2)_2$, $NR^2$, $PR^2$, $P(=O)R^2$, O, S, $S(=O)$, $S(=O)_2$, or, identically or differently, any combination of 2, 3, 4 or 5 of these divalent groups;

$R^1$ is on each occurrence, identically or differently, H, D, F, $C(=O)R^4$, CN, $Si(R^4)_3$, $N(Ar^1)_2$, $N(R^4)_2$, $P(=O)(R^4)_2$, O $Ar^1$, $S(=O)R^4$, $S(=O)_2R^4$, a straight-chain alkyl or alkoxy group having 1 to 20 C atoms, a branched or cyclic alkyl or alkoxy group having 3 to 20 C atoms, or an alkenyl or alkynyl group having 2 to 20 C atoms, wherein these groups are optionally substituted by one or more radicals $R^4$ and wherein one or more CH2 groups in these groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO, or $SO_2$, or an aromatic or heteroaromatic ring system having 5 to 30 aromatic ring atoms, which is optionally substituted by one or more radicals $R^4$, and wherein two or more radicals $R^1$ are optionally linked to one another so as to define a ring;

$R^2$ is on each occurrence, identically or differently, H, D, F, $C(=O)R^4$, CN, $Si(R^4)_3$, n $N(R^4)_2$, $P(=O)(R^4)_2$, $S(=O)R^4$, $S(=O)_2R^4$, a straight-chain alkyl or alkoxy group having 1 to 20 C atoms, a branched or cyclic alkyl or alkoxy group having 3 to 20 C atoms, or an alkenyl or alkynyl group having 2 to 20 C atoms, wherein these groups are optionally substituted by one or more radicals $R^4$ and wherein one or more $CH_2$ groups in these groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO, or $SO_2$, or an aromatic or heteroaromatic ring system having 5 to 30 aromatic ring atoms, which is optionally substituted by one or more radicals $R^4$, and wherein two or more radicals $R_2$ are optionally linked to one another so as to define a ring;

$R^3$ is on each occurrence, identically or differently, H, D, F, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms, a branched or cyclic alkyl or alkoxy group having 3 to 20 C atoms, or an alkenyl or alkynyl group having 2 to 20 C atoms, where these groups are optionally substituted by one or more radicals $R^4$ and wherein one or more CH2 groups in these groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO, or $SO_2$, or an aromatic or heteroaromatic ring system having 5 to 30 aromatic ring atoms, which is optionally substituted by one or more radicals $R^4$, and wherein two or more radicals $R^3$ are optionally linked to one another so as to define a ring;

$R^4$ is on each occurrence, identically or differently, H, D, F or an aliphatic, aromatic or heteroaromatic organic radical having 1 to 20 C atoms, wherein one or more H atoms are optionally replaced by D or F; and wherein two or more radicals $R^4$ are optionally linked to one another so as to define a ring.

2. The compound of claim 1, wherein X is on each occurrence, identically or differently, a divalent group selected from the group consisting of $C(R^2)_2$, $NR^2$, O, and S.

3. The compound of claim 1, wherein X is on each occurrence, identically or differently, a divalent group selected from the group consisting of $C(R^2)_2$ and $NR^2$.

4. The compound of claim 1, wherein $Ar^1$ is on each occurrence, identically or differently, an aromatic ring system having 6 to 12 aromatic ring atoms, which is optionally substituted by one or more radicals $R^3$.

5. The compound of claim 1, wherein $Ar^1$ is phenyl, which is optionally substituted by one or more radicals $R^3$.

6. The compound of claim 4, wherein $Ar^1$ is a phenyl group, which is optionally substituted by one or more radicals $R^3$, and wherein the bond to the group X and to the nitrogen atom on the phenyl group are in the meta position relative to one another.

7. The compound of claim 1, wherein the pyrene group is substituted by at least one radical $R^1$ which is not H.

8. The compound of claim 1, wherein the pyrene group is substituted by at least one radical $R^1$ which is selected from a straight-chain alkyl group having 1 to 8 C atoms or a branched or cyclic alkyl group having 3 to 8 C atoms, where the alkyl groups are optionally substituted by one or more radicals $R^4$, or from an aryl or heteroaryl group having 6 to 14 aromatic ring atoms, which is optionally substituted by one or more radicals $R^4$.

9. The compound of claim 1, wherein radicals $R_2$ on a group X which represent $C(R^2)_2$ or $Si(R^2)_2$ are selected from a straight-chain alkyl group having 1 to 8 C atoms or a branched or cyclic alkyl group having 3 to 8 C atoms, where the alkyl groups are optionally substituted by one or more radicals $R^4$, or from an aryl or heteroaryl group having 6 to 14 aromatic ring atoms, which is optionally substituted by one or more radicals $R^4$.

10. An oligomer, polymer, or dendrimer comprising one or more compounds of claim 1, wherein the bond(s) to the polymer, oligomer, or dendrimer may be located at any positions substituted by $R^1$, $R^2$, or $R^3$ of formulae (I-1), (I-2), or (I-3).

11. A formulation comprising at least one compound of claim 1 and at least one solvent.

12. An electronic device comprising at least one compound of claim 1, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

13. The electronic device of claim 12, wherein the electronic device is an organic electroluminescent device and wherein the compound of formulae (I-1), (I-2), or (I-3) is present as an emitting compound in an emitting layer.

14. A process for preparing a compound of claim 1, comprising at least one transition metal-catalysed coupling reaction.

* * * * *